US011458099B2

(12) United States Patent
Medina et al.

(10) Patent No.: US 11,458,099 B2
(45) Date of Patent: Oct. 4, 2022

(54) INHALABLE ANTIMICROBIAL PARTICLES AND METHODS OF MAKING THE SAME

(71) Applicant: The Penn State Research Foundation, University Park, PA (US)

(72) Inventors: Scott Hammond Medina, State College, PA (US); Andrew William Simonson, Kennett Square, PA (US)

(73) Assignee: The Penn State Research Foundation, University Park, PA (US)

( * ) Notice: Subject to any disclaimer, the term of this patent is extended or adjusted under 35 U.S.C. 154(b) by 183 days.

(21) Appl. No.: 16/619,490

(22) PCT Filed: Jun. 5, 2018

(86) PCT No.: PCT/US2018/035942
§ 371 (c)(1),
(2) Date: Dec. 5, 2019

(87) PCT Pub. No.: WO2018/226614
PCT Pub. Date: Dec. 13, 2018

(65) Prior Publication Data
US 2020/0179287 A1 Jun. 11, 2020

Related U.S. Application Data

(60) Provisional application No. 62/515,019, filed on Jun. 5, 2017.

(51) Int. Cl.
| *A61K 9/16* | (2006.01) |
| *A61K 38/10* | (2006.01) |
| *A61K 38/17* | (2006.01) |
| *A61P 31/06* | (2006.01) |
| *A61K 9/19* | (2006.01) |
| *A61K 31/131* | (2006.01) |
| *A61K 31/4245* | (2006.01) |
| *A61K 31/4409* | (2006.01) |
| *A61K 31/496* | (2006.01) |
| *A61K 31/4965* | (2006.01) |
| *A61K 31/7036* | (2006.01) |
| *A61K 31/704* | (2006.01) |
| *A61K 38/14* | (2006.01) |

(52) U.S. Cl.
CPC .......... *A61K 9/1658* (2013.01); *A61K 9/1652* (2013.01); *A61K 9/19* (2013.01); *A61K 31/131* (2013.01); *A61K 31/4245* (2013.01); *A61K 31/4409* (2013.01); *A61K 31/496* (2013.01); *A61K 31/4965* (2013.01); *A61K 31/704* (2013.01); *A61K 31/7036* (2013.01); *A61K 38/14* (2013.01); *A61P 31/06* (2018.01)

(58) Field of Classification Search
None
See application file for complete search history.

(56) References Cited

U.S. PATENT DOCUMENTS

| 5,811,124 A | 9/1998 | Fernandez et al. |
| 6,884,435 B1 | 4/2005 | O'Hagan et al. |
| 7,329,638 B2 | 2/2008 | Yang et al. |
| 8,343,475 B2 | 1/2013 | Hancock et al. |

FOREIGN PATENT DOCUMENTS

| KR | 2010134368 A | * 12/2010 |
| KR | 101096679 B1 | 12/2011 |

OTHER PUBLICATIONS

Palena, M. C., R. H. Manzo, and A. F. Jimenez-Kairuz. "Self-organized nanoparticles based on drug-interpolyelectrolyte complexes as drug carriers." Journal of Nanoparticle Research 14.6 (2012): 1-12. (Year: 2012).*
Silva, Joao P., et al. "Delivery of LLKKK18 loaded into self-assembling hyaluronic acid nanogel for tuberculosis treatment." Journal of Controlled Release 235 (2016): 112-124. (Year: 2016).*
Ramón-García, Santiago, et al. "Targeting *Mycobacterium tuberculosis* and other microbial pathogens using improved synthetic antibacterial peptides." Antimicrobial agents and chemotherapy 57.5 (2013): 2295-2303. (Year: 2013).*
Manca, Maria Letizia, et al. "Fabrication of polyelectrolyte multilayered vesicles as inhalable dry powder for lung administration of rifampicin." International journal of pharmaceutics 472.1-2 (2014): 102-109. (Year: 2014).*
Brown, Kelly L., and Robert EW Hancock. "Cationic host defense (antimicrobial) peptides." Current opinion in immunology 18.1 (2006): 24-30. (Year: 2006).*
Hancock, Robert EW, and Hans-Georg Sahl. "Antimicrobial and host-defense peptides as new anti-infective therapeutic strategies." Nature biotechnology 24.12 (2006): 1551-1557. (Year: 2006).*
Lankalapalli, S., and V. R. M. Kolapalli. "Polyelectrolyte complexes: A review of their applicability in drug delivery technology." Indian journal of pharmaceutical sciences 71.5 (2009): 481. (Year: 2009).*
Fjell, Christopher D., et al. "Designing antimicrobial peptides: form follows function." Nature reviews Drug discovery 11.1 (2012): 37-51. (Year: 2012).*
Lankalapalli, Srinivas, Krishna Chaitanya Routhu, and VS Vinai Kumar Tenneti. "Preparation and evaluation of vancomycin polyelectrolyte complex nanoparticles." Indian Journal of Nanoscience 2.8 (2014): 10-18. (Year: 2014).*

(Continued)

*Primary Examiner* — Bethany P Barham
*Assistant Examiner* — Peter Anthopolos
(74) *Attorney, Agent, or Firm* — Hodgson Russ LLP

(57) ABSTRACT

The present invention relates in part to novel drug delivery particles comprising an anionic polymer matrix and a cationic polymer, wherein the anionic polymer matrix and cationic polymer together form drug delivery particles bound by electrostatic interactions and wherein the drug delivery particles comprise at least one biologically active agent. The invention also relates in part to a method of treating a mycobacterial infection using said drug delivery particles, and a method of making said drug delivery particles.

10 Claims, 15 Drawing Sheets

Specification includes a Sequence Listing.

(56) References Cited

OTHER PUBLICATIONS

Palena, María Celeste, et al. "Self-organized drug-interpolyelectrolyte nanocomplexes loaded with anionic drugs. Characterization and in vitro release evaluation." Journal of Drug Delivery Science and Technology 30 (2015): 45-53. (Year: 2015).*

Abedinzadeh, Maria, Mahdieh Gaeini, and Soroush Sardari. "Natural antimicrobial peptides against *Mycobacterium tuberculosis*." Journal of Antimicrobial Chemotherapy 70.5 (2015): 1285-1289. (Year: 2015).*

Water, Jorrit J., et al. "Hyaluronic acid-based nanogels produced by microfluidics-facilitated self-assembly improves the safety profile of the cationic host defense peptide novicidin." Pharmaceutical research 32.8 (2015): 2727-2735. (Year: 2015).*

Kulkarni, Abhijeet D., et al. "Polyelectrolyte complexes: mechanisms, critical experimental aspects, and applications." Artificial cells, nanomedicine, and biotechnology 44.7 (2016): 1615-1625. (Year: 2016).*

Hancock, Robert EW, Evan F. Haney, and Erin E. Gill. "The immunology of host defence peptides: beyond antimicrobial activity." Nature Reviews Immunology 16.5 (2016): 321-334. (Year: 2016).*

Arranz-Trullén, Javier, et al. "Host antimicrobial peptides: the promise of new treatment strategies against tuberculosis." Frontiers in immunology 8 (2017): 1499. (Year: 2017).*

Marciel, Amanda B., et al. "Bulkand nanoscale polypeptide based polyelectrolyte complexes." Advances in colloid and interface science 239 (2017): 187-198. (Year: 2017).*

Ramadoss et al., "Small molecule inhibitors of trans-translation have broad-spectrum antibiotic activity," PNAS, 2013, vol. 110, No. 25, pp. 10282-10287.

Ramon-Garcia et al., "Targeting *Mycobacterium tuberculosis* and Other Microbial Pathogens Using Improved Synthetic Antibacterial Peptides," Antimicrobial Agents and Chemotherapy, 2013, vol. 57, No. 5, pp. 2295-2303.

Zamani et al., "Advances in drug delivery via electrospun and electrosprayed nanomaterials," International Journal of Nanomedicine, 2013, vol. 8, pp. 2997-3017.

\* cited by examiner

INHALABLE ANTIMICROBIAL PARTICLES AND METHODS OF MAKING THE SAME

CROSS-REFERENCE TO RELATED APPLICATIONS

The present application is a 35 U.S.C. § 371 national phase application from, and claiming priority to, International Application No. PCT/US2018/035942, filed Jun. 5, 2018, which claims priority under 35 U.S.C. § 119(e) to U.S. Provisional Patent Application Ser. No. 62/515,019, filed Jun. 5, 2017, all of which are incorporated herein by reference in their entireties.

BACKGROUND OF THE INVENTION

Despite effective treatments for tuberculosis (TB), it remains a leading cause of morbiditiy and mortality around the world. Presently, standard TB treatment regiments require patients to complete a six-month course of a multi-drug cocktail taken daily under the direct observation of a healthcare worker. This burden ultimately leads to inappropriate drug use and early termination of treatment, collectively contributing to the widespread emergence of multi drug-resistant TB (MDR-TB) and extensively drug-resistant TB (XDR-TB) strains. Although TB vaccines are available and provide limited defense to young children, they are all but ineffective in preventing highly contagious adult pulmonary TB.

Tuberculosis (TB), caused by *Mycobacterium tuberculosis* (MTb), remains one of the leading causes of mortality worldwide, afflicting more than 9 million new people per year and causing more than 1.5 million deaths (Zumla, et al., Nat. Rev. Drug Discov. 2013, 12 (5), 388-404; Horsburgh, et al., N. Engl. J. Med. 2015, 373 (22), 2149-2160). Importantly, an estimated 2 billion individuals are infected with MTb in an asymptomatic latent stage, and are at risk of re-emergence of the disease. Despite the prevalence of TB infection, drug-susceptible TB can be effectively treated through directly observed therapy (DOT) in which patients receive a multi-drug oral cocktail (rifampicin, isoniazid, pyrazinamide and ethambutol) that is taken daily for 6 months. If completed this regimen leads to cure rates that are >95%. However, several issues complicate current therapy, including drug intolerance and toxicity, drug-drug interactions and the burdensome length of treatment required to achieve a re-lapse free cure (Chan and Iseman, Curr. Opin. Infect. Dis. 2008, 21 (6), 587-595). As a result, patients are routinely non-compliant, either taking drugs inappropriately outside of DOT or terminating treatment early (Munro, et al., PLoS Med. 2007, 4 (7), e238). These challenges have contributed to the widespread emergence of multi drug-resistant TB (MDR-TB) and extensively drug-resistant TB (XDR-TB) strains, that require 'individualized' treatments using second- and third-line antibiotics that are more expensive, have significantly increased toxicities and must be administered for up to 24 months (Gandhi, et al., The Lancet 2010, 375 (9728), 1830-1843; Keshavjee and Farmer, N. Engl. J. Med. 2012, 367 (10), 931-936).

To complicate matters, MTb can reside within niche environments in the lung where they are protected from the action of antibiotics (Ramakrishnan, Nat. Rev. Immunol. 2012, 12 (5), 352-366). For example, mycobacteria colonizing the alveolar epithelium are phagocytosed by lung macrophages and trafficked to the phagolysosome. However, MTb has evolved mechanisms to inhibit phagosome maturation and avoid hydrolytic destruction, ultimately allowing them to replicate unperturbed in the infected host cell (Russell, et al., Nat. Immunol. 2009, 10 (9), 943-948). In an attempt to contain the infection, the immune system sequesters MTb and infected macrophages within granulomas that, counter-productively, limits the diffusion of antibiotics into the tissue and creates an anaerobic environment that renders MTb dormant and phenotypically resistant to standard drugs (Horsburgh, et al., N. Engl. J. Med. 2015, 373 (22), 2149-2160). These challenges, along with the spread of drug-resistant disease, has created a renewed urgency for new anti-TB therapeutic candidates that can 1) elicit their activity on targets distinct from conventional antibiotics, and thus are effective against drug-resistant bacteria, 2) kill both proliferative and non-replicating dormant MTb, and 3) are sufficiently potent to shorten the course of treatment. Conversely, current TB drugs are still effective but require more efficient delivery strategies to be operational (Griffiths, et al., Nat. Rev. Microbiol. 2010, 8 (11), 827-834). Thus, carrier systems that can co-deliver new classes of anti-TB agents with standard antibiotics, while providing long-term drug release, represents an effective and compliant strategy in the treatment of drug-susceptible and -resistant TB.

Replacing the oral administration of free antibiotics with inhalable drug-loaded microparticles is an attractive strategy for TB therapy as it increases the local concentration of drug at the infection site, thereby enhancing potency and minimizing off-target toxicity, while controllably releasing the cargo to afford reduced frequency of dosing (Griffiths, et al., Nat. Rev. Microbiol. 2010, 8 (11), 827-834). Traditional approaches have utilized chemically-crosslinked poly(lactic-co-glycolic acid) (PLGA) polymer microspheres, in which antibiotics are encapsulated within the porous particle matrix. Cell- and animal-based studies show that PLGA particles prolong therapeutically relevant concentrations of loaded antibiotics within the plasma, and allow for preferential accumulation of drug within infected macrophages (Sosnik, et al., Adv. Drug Delivery Rev. 2010, 62 (4), 547-559; Hirota, et al., J. Controlled Release 2010, 142 (3), 339-346; O'Hara and Hickey, Pharm. Res. 2000, 17 (8), 955-961; Suarez, et al., Pharm. Res. 2001, 18 (9), 1315-1319). Despite the popularity of this approach it is not without significant challenges. The organic solvents and chemical cross-linkers used to synthesize PLGA microspheres are toxic and can induce severe allergic reactions in patients, thus limiting their clinical utility (Griffiths, et al., Nat. Rev. Microbiol. 2010, 8 (11), 827-834).[9] More importantly, these technologies deliver traditional TB antibiotics and thus do not effectively circumvent drug resistance.

Modern high throughput screening campaigns have identified an abundance of biochemical probes and therapeutic candidates with unprecedented specificity and potency. These agents, if successfully translated into the clinic, could transform strategies in precision medicine and lead to the design of highly selective antimicrobials. Yet, many potentially efficacious lead molecules are abandoned due to poor water solubility, low bioavailability, rapid systemic clearance and off-target biodistribution to healthy tissues leading to dose-limiting adverse events. Even many clinically approved pharmaceutics must be formulated with toxic adjuvants and/or excipients that can compound the side effects of the active agent.

Incorporation of diagnostic or therapeutic cargo into bioresponsive nanomaterials, such as a polymer or lipid-based nanoparticle, can address these challenges by improving the pharmacologic and therapeutic properties of loaded agents when parenterally administered. Chemical ligation or physical encapsulation of biomolecular cargo within a nano-carrier matrix leads to enhanced aqueous solubility, improved serum stability and affords preferential localization to diseased tissues through size-dependent passive targeting. Considerable efforts are now being made to develop bioresponsive nano-scale vehicles to improve the transport of sensitive protein and nucleic-acid based agents for genome editing, biotherapy and biosensing applications. While a number of 'smart' delivery systems have been designed to address this need, successful translation of these platforms into the clinic has remained elusive due to their significant chemical complexity, substantial cost to scale and toxicity of the matrix constituents upon carrier degradation in physiologic environments.

There is need in the art for novel drug delivery formulations. The present invention satisfies this unmet need.

SUMMARY OF THE INVENTION

The present invention relates in part to a plurality of drug delivery particles, comprising an anionic polymer matrix; and a cationic polymer; wherein the anionic polymer matrix and cationic polymer together form drug delivery particles bound by electrostatic interactions; and wherein the drug delivery particles comprise at least one biologically active agent. In one embodiment, the anionic polymer matrix comprises an anionic polymer selected from the group consisting of alginic acid, arabic acid, polygalacturonic acid, poly(glucuronic acid), hyaluronic acid, heparin, N-acetyl heparin, carboxymethylcellulose, chondroitin sulfate, chondroitin sulfate B, chitin, O- or N-sulfochitosan, CM-dextran, dextran sulfate, and pectin. In one embodiment, the anionic polymer matrix comprises hyaluronic acid. In one embodiment, the cationic polymer is a polypeptide. In one embodiment, the cationic peptide is poly-L-lysine. In one embodiment, the cationic peptide comprises a sequence selected from the group consisting of WKWLKKWIK, ILRWKWRWWRWRR, KRWWKWWRR, and RRWWRWVVW. In one embodiment, the zeta potential of the particles is negative. In one embodiment, the at least one biologically active agent is selected from the group consisting of an antimycobacterial agent, an antimicrobial agent, an antiviral agent, an anticancer agent, and a biologic. In one embodiment, the at least one biologically active agent is selected from the group consisting of rifampicin, isoniazid, ethambutol, pyrazinamide, streptomycin, 4-chloro-N-(5-(4-fluorophenyl)-1,3,4-oxadiazol-2-yl)benzamide, vancomycin, and doxorubicin. In one embodiment, the drug delivery particles further comprise at least one pharmaceutically acceptable carrier.

The present invention also relates in part to a dry powder formulation comprising the particles of the invention, and a method of treating a mycobacterial infection in a subject in need thereof, the method comprising the step of administering to the subject a formulation comprising the particles of the invention.

The present invention also relates in part to A method for the manufacture of drug delivery particles, the method comprising the steps of: providing a sample solution comprising at least one anionic polymer; providing a bath solution comprising at least one cationic polymer; electrospraying the sample solution into the bath solution to form a drug delivery particle solution; and isolating a plurality of drug delivery particles from the drug delivery particle solution; wherein at least one of the sample solution, the bath solution, or the solution of drug delivery particles further comprises at least one biologically active agent. In one embodiment, the step of isolating a plurality of drug delivery particles from the drug delivery particle solution comprises the step of centrifuging the drug delivery particle solution and removing the supernatant. In one embodiment, the step of isolating a plurality of drug delivery particles from the drug delivery particle solution further comprises the step of lyophilizing the drug delivery particles. In one embodiment, the step of electrospraying the sample solution into the bath solution to form a drug delivery particle solution further comprises the step of incubating the drug delivery solution for at least one hour at least 37° C. In one embodiment, the bath solution comprises the biologically active agent. In one embodiment, the at least one anionic polymer comprises hyaluronic acid. In one embodiment, the at least one cationic polymer comprises poly-L-lysine or an antimicrobial polypeptide. In one embodiment, the electrospray voltage is between about 10 kV and about 50 kV.

BRIEF DESCRIPTION OF THE DRAWINGS

The following detailed description of various embodiments of the invention will be better understood when read in conjunction with the appended drawings. For the purpose of illustrating the invention, there are shown in the drawings illustrative embodiments. It should be understood, however, that the invention is not limited to the precise arrangements and instrumentalities of the embodiments shown in the drawings.

FIG. 7A is a plot comparing the activity of non-drug-loaded microgels against gram-negative bacteria M. smeg to the activity against mammalian lung epithelial cell controls. FIG. 7B is a plot showing the controlled release of three exemplary cargos from model particle formulations.

FIGS. 9A-9D, depicts physical characteristics of exemplary drug delivery particles. FIG. 9A is a plot of particle size as measured using dynamic light scattering (DLS). FIG. 9B is an image of the electrospray bath solution before (left) and immediately after (right) synthesis of exemplary drug delivery particles. The rapid change in solution turbidity illustrates the high yield production of particles, which remain colloidally stable. FIG. 9C is a plot of a Zeta potential analysis of exemplary drug delivery particles. The negative surface charge suggests a core-shell particle architecture in which an anionic HA corona surrounds a cationic PLL core (inset). FIG. 9D is a plot of particle diameter as a function of N:P ratio for exemplary drug delivery particles of N:P ratio of 1:1 to 15:1.

FIGS. 10A-10E, depicts physicochemical characteristics of exemplary drug delivery particles. FIG. 10A is a plot of particle size, as measured by DLS, under various applied electrospray voltages. FIG. 10B is a plot of particle size at various N:P ratios, as measured by DLS. FIG. 10C is a plot depicting the zeta potential of particles prepared at N:P ratios of 5 and 10. FIG. 10D is a chart showing the stability of particle size when stored in DI water. FIG. 10E is a plot of particle size following loading of the model protein GFP ($NG_{GFP}$), the chemotherapeutic agent DOX ($NG_{DOX}$), or the antibiotic VAN ($NG_{VAN}$), as determined by DLS. Unloaded NG shown for reference.

FIGS. 11-11, depicts the effects of prolonged exposure of exemplary drug delivery particles to physiologic media. FIG. 11A is a plot of relative nanogel swelling in physiologic media at N:P ratios of 1:1 to 15:1. Dotted lines signify disruption of particle integrity as indicated by loss of DLS signal. Note, N:P=1 nanogels rapidly degrade between 0 and 0.5 hours. FIG. 11B depicts scanning electron micrographs (SEMs) of exemplary drug delivery particles nanogels before (top) and after (bottom) 18 hours of swelling; (scale bar=500 um) FIG. 11C is a plot of time to particle degradation as a function of N:P ratio.

FIGS. 12A-12D, depicts the utility of exemplary drug delivery particles for drug delivery applications. FIG. 12A is a schematic showing the various loading methods available for the encapsulation of molecular cargoes within exemplary drug delivery particles. Vancomycin (VAN, blue) is suspended in the HA sample solution, while Green fluorescent protein (GFP, green) is present in the bath solution, leading to their encapsulation during nanogel assembly. Doxorubicin (DOX, red) is incubated with pre-formed drug delivery particles, leading to its adsorption within the particle amphiphilic matrix. FIG. 12B is a plot of the fraction of cargo released as a function of time. FIG. 12C is a plot of the zeta potential analysis of un-loaded nanogels (NG) compared to formulations encapsulating the various molecular cargoes. FIG. 12D is an illustration of molecular cargo localization of GFP (green), VAN (blue) or DOX (red) within exemplary drug delivery particles.

FIGS. 13A-13C, depicts the intake of GFP from GFP-loaded drug delivery particles by cancer cells. FIG. 13A shows merged confocal microscopy images of Hoechst (blue) and GFP (green) fluorescent channels for A549 lung carcinoma cells treated with free GFP, or GFP-loaded nanogels without ($NG_{GFP}$) and with co-incubation of excess HA ($NG_{GFP}$+HA). (60× magnification; scale bar=10 μm). FIG. 13B is a chart of the quantitation of average GFP fluorescence per cell for each treatment condition (n=15; p<0.01). FIG. 13C depicts fluorescent confocal microscopy images of A549 cells treated with free GFP or $NG_{GFP}$, and co-stained with the endosomal marker texas-red labeled transferrin (TransferrinTR). Individual fluorescence channels and merged images shown (60× magnification; scale bar=10 μm).

FIGS. 14A and 14B, depicts the results of cytoxicity studies against potential therapeutic targets. FIG. 14A depicts the antibacterial effect of non-drug-loaded drug delivery particles against the gram-negative pathogen M. smeg. compared to mammalian lung epithelial cell controls (A549). FIG. 14B shows the cytotoxicity of free DOX, DOX-loaded nanogels ($NG_{DOX}$) or the empty nanogel carrier (NG) against A549 lung carcinoma cells (chart and table) and the multi-drug resistant NCI/ADR-RES ovarian cancer cell line (table only). Table results are shown as the $IC_{50}$ of DOX, or the equivalent concentration of drug loaded into nanogels, as well as the corresponding amount of the carrier (represented as DOX|NG carrier). NA=not applicable. *indicates maximum concentration tested.

FIG. 15A is a plot of the viability of human umbilical vein endothelial cells (HUVEC) as a function of drug delivery particle concentration. FIG. 15 B is a plot of bovine red blood cell hemolysis percentage following a 24 hour incubation with increasing concentrations of the empty nanogel carrier. TX=Triton X-100 positive control.

DETAILED DESCRIPTION

Figure 1:
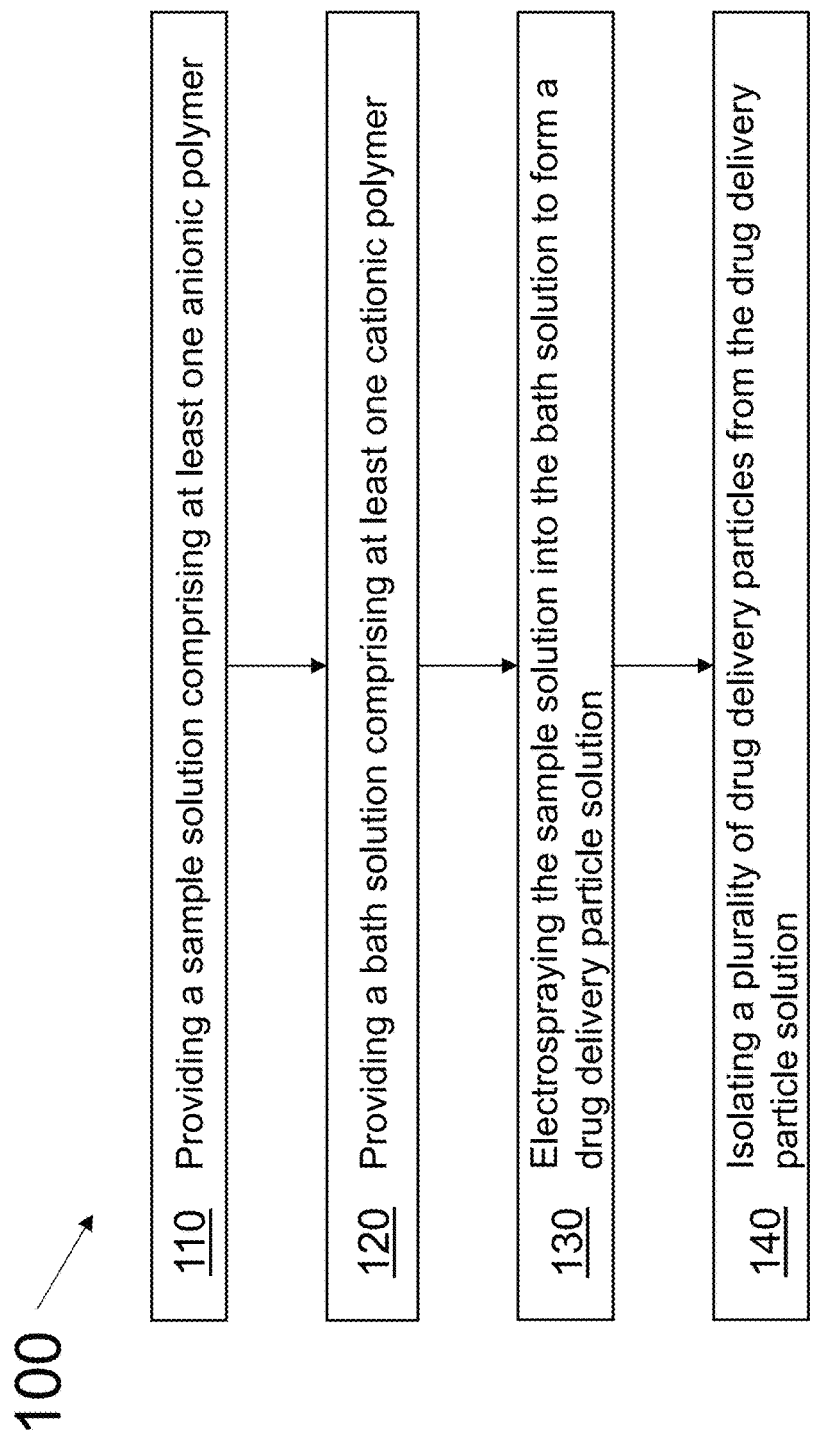
FIG. 1 is a flowchart of an exemplary method for the production of an antimicrobial formulation.

It is to be understood that the Figures and descriptions of the present invention have been simplified to illustrate elements that are relevant for a clear understanding of the present invention, while eliminating, for the purpose of clarity, many other elements found in antimicrobial compositions and methods of making. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

As used herein, each of the following terms has the meaning associated with it in this section. Unless defined otherwise, all technical and scientific terms used herein generally have the same meaning as commonly understood by one of ordinary skill in the art to which this invention belongs.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human. As used herein, a subject is preferably a mammal such as a non-primate (e.g., cows, pigs, horses, cats, dogs, rats, etc.) and a primate (e.g., monkey and human), most preferably a human.

"Parenteral" administration of a composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of such diseases.

To "treat" a disease as the term is used herein, means to reduce the frequency or severity of at least one sign or symptom of a disease or disorder experienced by a subject.

As used herein, the term "attached to" refers to attaching two chemical groups through a chemical bond, for example a covalent bond or a non-covalent bond.

As used herein, the terms "amide," "amide group," or "amido group," employed alone or in combination with other terms, means, unless otherwise stated, a chemical group containing one or more amino groups. In one example, the amide group is represented by structure of —C(O)NR$_a$R$_b$, wherein the carbon atom may optionally be substituted with sulfate or phosphate atom; and wherein, in some embodiments of the invention, R$_a$ and R$_b$ are hydrogen.

The articles "a" and "an" are used herein to refer to one or to more than one (i.e. to at least one) of the grammatical object of the article. By way of example, "an element" means one element or more than one element.

As used herein, the term "about" will be understood by persons of ordinary skill in the art and will vary to some extent depending on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Drug Delivery Particles

According to one aspect, the present invention relates to a plurality of drug delivery particles comprising an anionic polymer matrix; and a cationic polymer; wherein the anionic polymer matrix and cationic polymer together form drug delivery particles bound by electrostatic interactions; and wherein the drug delivery particles comprise at least one biologically active agent.

The anionic polymer matrix comprises any polymer having an overall negative charge. Exemplary polymers include, but are not limited to, synthetic polymers such as polyacrylates, poly(4-styrenesulfonate), poly(vinyl sulfate), and poly (vinylphosphonic acid), poly(vinylphosphate), polymetaphosphate; polypeptides having an overall negative charge and comprising a plurality of amino acids that are negatively charged at physiological conditions, such as, but not limited to, poly(glutamic acid), poly(γ-glutamic acid), poly(aspartic acid), poly(β-aspartic acid), and copolymers and block copolymers thereof; carbohydrate biopolymers such as alginic acid, arabic acid, polygalacturonic acid, poly(glucuronic acid), hyaluronic acid, heparin, N-acetyl heparin, carboxymethylcellulose, chondroitin sulfate, chondroitin sulfate B, chitin, O- or N-sulfochitosan, CM-dextran, dextran sulfate, pectin, ribonucleic acid (RNA), deoxyribonucleic acid (DNA); lignins and lignin-derived polymers; and combinations, co-polymers, and block-copolymers thereof. In some embodiments, the anionic polymer is a copolymer or a block copolymer. In some embodiments, the copolymer or block copolymer further comprises at least one neutral monomer. In some embodiments, the copolymer or block copolymer further comprises at least one cationic monomer. In one embodiment, the anionic polymer comprises hyaluronic acid. In one embodiment, the anionic polymer comprises alginic acid. In one embodiment, the anionic polymer comprises a polypeptide having an overall negative charge. In one embodiment, the anionic polymer comprises polygalacturonic acid. In one embodiment, the anionic polymer comprises polyglucoronic acid. One of ordinary skill in the art would appreciate that the overall negative charge refers to the backbone/framework of the polymer, and that the polymer necessarily comprises positively-charged counterions, such as but not limited to, lithium, sodium, potassium, or ammonium ions.

There is no particular limit to the size or length of the anionic polymer. In one embodiment, the anionic polymer has an average molecular weight between about 1 kDa and about 1,000 kDa. In one embodiment, the anionic polymer has an average molecular weight of about 1 kDa. In one embodiment, the anionic polymer has an average molecular weight of about 10 kDa. In one embodiment, the anionic polymer has an average molecular weight of about 100 kDa. In one embodiment, the anionic polymer has an average molecular weight of about 1,000 kDa.

The cationic polymer can be any polymer having an overall positive charge. One of ordinary skill in the art would appreciate that the overall positive charge refers to the backbone/framework of the polymer, and that the polymer necessarily comprises negatively-charged counterions, such as but not limited to, acetate, fluoride, chloride, bromide, and iodide anions. Exemplary cationic polymers include, but are not limited to, quaternary ammonium-containing synthetic polymers such as poly(methacryloxyethyldimethylbenzylammonium chloride) (poly(DMAEM.BzCl)), poly(methacryloxyethyldiethylmethylammonium chloride) (poly(DEAEM.MeCl)), poly(acrylamido(2-methylbutyl) trimethylammonium chloride) (poly(AMBTAC)), poly (methacryloxyethyltrimethylammonium chloride) (poly (MOTAC.MeCl)), poly(acryloxyethyltrimethylammonium chloride) (poly(AETAC.MeCl)), poly(acrylamidopropyltrimethylammonium chloride) (poly(APTAC)), poly(methacrylamidopropyltrimethylammonium chloride) (poly (MAPTAC)), poly(methyloyloxyethyltrimethylammonium chloride) (poly(METAC)), poly(methyloyloxyethyltrimethylammonium methyl sulfate) (polyMETAMS), poly(acryloyloxyethyltrimethylammonium chloride (poly(AETAC)), poly(2-methacryloxyethyltrimethylammonium chloride) (poly(MADQUAT)), poly(dimethyldiallylammonium chloride) (poly(DMDAAC)), poly(triallylmethylammonium chloride) (poly(TAMAC)), poly(allylamine hydrochloride), polybrene, polyethyleneimine (PEI), ionene polymers, poly (N-vinylimidazole), poly(N'-alkyl-N-vinylimidazoliums), polyquaternium-1 through -47, DEAE-dextran, and combinations, copolymers, and block copolymers thereof.

In one embodiment, the cationic polymer comprises a polypeptide. In one embodiment, the polypeptide has an overall positive charge. Such polypeptides comprise a plurality of amino acids that are positively charged at physiological conditions, including homopeptides such as, but not limited to, α- or ε-poly-L-lysine, poly-L-histidine, α- or δ-poly-L-ornithine, poly-L-arginine; polypeptides further comprising anionic or neutral amino acids, such as histone, collagen; and synthetic or natural peptides.

In one embodiment, the cationic polymer comprises a polypeptide having a chemical modification at a terminal residue. In one embodiment, the cationic polymer comprises a polypeptide having a modification the N-terminus. In one embodiment, the cationic polymer comprises a polypeptide having a modification at the C-terminus. In one embodiment, the cationic polymer comprises a polypeptide having a free carboxylate (—O⁻) or carboxylic acid (—OH) at the C-terminus. In one embodiment, the cationic polymer comprises a polypeptide having an amido group (—NH$_2$) at the C-terminus. In one embodiment, the cationic polymer comprises a polypeptide comprising a sequence selected from the group consisting of FFIYVWRRR (SEQ ID NO:1), FIKWKFRWWKWRK (SEQ ID NO:2), HQFRFRFRVRRK (SEQ ID NO:3), ILPWKWRWWKWRR (SEQ ID NO:4), ILRWKWRWWRWRR (SEQ ID NO:5), IRMRIRVLL (SEQ ID NO:6), KFKWWRMLI (SEQ ID NO:7), KIWWWWRKR (SEQ ID NO:8), KRKKRFKWW (SEQ ID NO:9), KRRWRIWLV (SEQ ID NO:10), KRWHWWRRHWVVW (SEQ ID NO:11), KRWWKWWRR (SEQ ID NO:12), KRWWRKWWR (SEQ ID NO:13), KRWWWWRFR (SEQ ID NO:14), KWKWWWRKI (SEQ ID NO:15), LKRRWKWWI (SEQ ID NO:16), LRFILWWKR (SEQ ID NO:17), LRRWIRIRW (SEQ ID NO:18), NWRKLYRRK (SEQ ID NO:19), RIKRWWWWR (SEQ ID NO:20), RIRRWKFRW (SEQ ID NO:21), RKFRWWVIR (SEQ ID NO:22), RKWKIKWYW (SEQ ID NO:23), RLKRWWKFL (SEQ ID NO:24), RLRRIVVIRVFR (SEQ ID NO:25), RLWRIVVIRVKR (SEQ ID NO:26), RLWWKIWLK (SEQ ID NO:27), RLWWWWRRK (SEQ ID NO:28), RQRRVVIWW (SEQ ID NO:29), RRRIKIRWY (SEQ ID NO:30), RRRWWKLMM (SEQ ID NO:31), RRWKIVVIRWRR (SEQ ID NO:32), RRWRVIVKW (SEQ ID NO:33), RRWWKWWWR (SEQ ID NO:34), RRWWRWVVW (SEQ ID NO:35), RRYHWRIYI (SEQ ID NO:36), RTKKWIVWI (SEQ ID NO:37), RWRRKWWWW (SEQ ID NO:38), RWRWWWRVY (SEQ ID NO:39), RWWIRIRWH (SEQ ID NO:40), RWWRKIWKW (SEQ ID NO:41), RWWRWRKWW (SEQ ID NO:42), VRLRIRVRVIRK (SEQ ID NO:43), WFKMRWWGR (SEQ ID NO:44), WKIVFWWRR (SEQ ID NO:45), WKWLKKWIK (SEQ ID NO:46), WKWRVRVTI (SEQ ID NO:47), WRKFWKYLK (SEQ ID NO:48), YKFRWRIYI (SEQ ID NO:49), YRLRVKWKW (SEQ ID NO:50), and combinations and/or C-terminal amido variants thereof.

Exemplary C-terminal amido-modified peptides include, but are not limited to, ILRWKWRWWRWRR-NH$_2$ (SEQ ID NO:51), KRWHWWRRHWVVW-NH$_2$ (SEQ ID NO: 52), KRWWKWWRR-NH$_2$ (SEQ ID NO:53), RRWWRWVVW-NH$_2$ (SEQ ID NO:54), and WKWLKKWIK-NH$_2$ (SEQ ID NO:55).

In some embodiments, the cationic polypeptide is an antimicrobial peptide. In some embodiments, the cationic peptide is an antimycobacterial peptide. In one embodiment, the cationic polypeptide comprises the sequence ILRWKWRWWRWRR (SEQ ID NO:5), KRWHWWRRHWVVW (SEQ ID NO:11), KRWWKWWRR (SEQ ID NO:12), RRWWRWVVW (SEQ ID NO:35), or WKWLKKWIK (SEQ ID NO:46).

In one embodiment, the cationic polymer comprises a polypeptide having a label at the C-terminus. In one embodiment, the label is selected from the group consisting of an affinity label molecule, a photoaffinity label, a dye, a chromophore, a fluorescent molecule, a phosphorescent molecule, a chemiluminescent molecule, an energy transfer agent, a photocrosslinker molecule, a redox-active molecule, an isotopic label molecule, a spin label molecule, a metal chelator, a metal-comprising moiety, a heavy atom-comprising-moiety, a radioactive moiety, a contrast agent molecule, a MRI contrast agent, an isotopically labeled molecule, a PET agent, a polypeptide, a cell penetrating polypeptide, a carbohydrate, a polynucleotide, a peptide nucleic acid, a fatty acid, a lipid, biotin, a biotin analogue, a polymer, a small molecule, a drug or drug candidate, a cytotoxic molecule, a solid support, a surface, a resin, a nanoparticle, a quantum dot and any combination thereof.

The size/length of the cationic polymer is not particularly limited. In one embodiment, the cationic polymer comprises about 10 monomeric repeating units. In one embodiment, the cationic polymer comprises about 20 monomeric repeating units. In one embodiment, the cationic polymer comprises about 30 monomeric repeating units. In one embodiment, the cationic polymer comprises about 50 monomeric repeating units. In one embodiment, the cationic polymer comprises about 100 monomeric repeating units. In one embodiment, the cationic polymer comprises about 250 monomeric repeating units. In one embodiment, the cationic polymer comprises about 400 monomeric repeating units. In one embodiment, the cationic polymer comprises about 800 monomeric repeating units.

In some embodiments, the cationic polymer is a cationic peptide. The peptide of the present invention may be made using chemical methods. For example, peptides can be synthesized by solid phase techniques (Roberge J Y et al (1995) Science 269: 202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer. Representative methods for preparing the peptides of the invention are provided in Example 4-6.

The invention should also be construed to include any form of a peptide having substantial homology to a peptide disclosed herein. Preferably, a peptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of a peptide disclosed herein.

The peptide may alternatively be made by recombinant means or by cleavage from a longer polypeptide. The composition of a peptide may be confirmed by amino acid analysis or sequencing.

The variants of the peptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two peptides is determined by comparing the amino acid sequence and its conserved amino acid substitutes of one polypeptide to a sequence of a second polypeptide. Variants are defined to include peptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence. The present invention includes amino acid sequences that are at least 60%, 65%, 70%, 72%, 74%, 76%, 78%, 80%, 90%, or 95% similar or identical to the original amino acid sequence. The degree of identity between two peptides is determined using computer algorithms and methods that are widely known for the persons skilled in the art.

The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

The peptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or Xenopus egg extracts (U.S. Pat. No. 6,103,489) to a standard translation reaction.

The peptides of the invention may include unnatural amino acids formed by post-translational modification or by introducing unnatural amino acids during translation. A variety of approaches are available for introducing unnatural amino acids during protein translation.

A peptide or protein of the invention may be conjugated with other molecules, such as proteins, to prepare fusion proteins. This may be accomplished, for example, by the synthesis of N-terminal or C-terminal fusion proteins provided that the resulting fusion protein retains the functionality of a peptide of the invention.

A peptide or protein of the invention may be phosphorylated using conventional methods such as the method described in Reedijk et al. (The EMBO Journal 11(4):1365, 1992).

Cyclic derivatives of the peptides of the invention are also part of the present invention. Cyclization may allow the peptide to assume a more favorable conformation for association with other molecules. For example, cyclization may allow the peptide to assume a more favorable conformation for association with a target protein. Accordingly, cyclization may result in improved binding affinity and specificity toward the target protein. Cyclization may also confer to the peptide beneficial properties such as increased resistance against proteolysis, increased cell permeability, and/or more favorable pharmacokinetic properties such as oral bioavailability, reduced clearance, and the like. In one embodiment, the cyclization of a peptide of the invention stabilizes the peptide into an α-helical conformation.

Cyclization may be achieved using techniques known in the art. These methods include the use of covalent inter-side-chain linkages such as disulfide bonds (Jackson, King et al. 1991), lactam (Osapay and Taylor 1992), thioether (Brunel and Dawson 2005) or triazole (Scrima, Le Chevalier-Isaad et al. 2010; Kawamoto, Coleska et al. 2012) bridges, 'hydrocarbon staples' (Blackwell and Grubbs 1998; Schafmeister, Po et al. 2000; Bernal, Wade et al. 2010), and cysteine cross-linking moieties (Zhang, Sadovski et al. 2007; Muppidi, Wang et al. 2011; Jo, Meinhardt et al. 2012; Spokoyny, Zou et al. 2013). Another known approach for stabilization of α-helical peptides involves the introduction of so-called 'hydrogen bond surrogates', i.e. hydrocarbon linkages replacing an N-terminal i/i+4 hydrogen bond (Wang, Liao et al. 2005). Any of these methods, or combination thereof, can be applied to stabilize the α-helical conformation of PGC1β, PGC1α-, or PRC-derived peptides for the purpose of developing inhibitors of the interaction between CBP80 and members of the PGC1 family of co-activators.

Other methods of cyclization disulfide bonds which may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

The invention also relates to peptides comprising a peptide fused to, or integrated into, a target protein, and/or a targeting domain capable of directing the chimeric protein to a desired cellular component or cell type or tissue. The chimeric proteins may also contain additional amino acid sequences or domains. The chimeric proteins are recombinant in the sense that the various components are from different sources, and as such are not found together in nature (i.e., are heterologous).

In one embodiment, the targeting domain can be a membrane spanning domain, a membrane binding domain, or a sequence directing the protein to associate with for example vesicles or with the nucleus. In one embodiment, the targeting domain can target a peptide to a particular cell type or tissue. For example, the targeting domain can be a cell surface ligand or an antibody against cell surface antigens of a target tissue (e.g., bone, regenerating bone, degenerating bone, cartilage). A targeting domain may target the peptide of the invention to a cellular component.

A peptide of the invention may be synthesized by conventional techniques. For example, the peptides or chimeric proteins may be synthesized by chemical synthesis using solid phase peptide synthesis. These methods employ either solid or solution phase synthesis methods (see for example, J. M. Stewart, and J. D. Young, Solid Phase Peptide Synthesis, $2^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis). By way of example, a peptide of the invention may be synthesized using 9-fluorenyl methoxycarbonyl (Fmoc) solid phase chemistry with direct incorporation of phosphothreonine as the N-fluorenylmethoxy-carbonyl-O-benzyl-L-phosphothreonine derivative.

N-terminal or C-terminal fusion proteins comprising a peptide or chimeric protein of the invention conjugated with other molecules may be prepared by fusing, through recombinant techniques, the N-terminal or C-terminal of the peptide or chimeric protein, and the sequence of a selected protein or selectable marker with a desired biological function. The resultant fusion proteins contain the peptide fused to the selected protein or marker protein as described herein. Examples of proteins which may be used to prepare fusion proteins include immunoglobulins, glutathione-S-transferase (GST), hemagglutinin (HA), and truncated myc.

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

In one embodiment, at least one of the anionic polymer and the cationic polymer is registered as a GRAS (generally recognized as safe) substance. In one embodiment, at least one of the anionic polymer and the cationic polymer is degraded by bacterial enzymes. In one embodiment, at least one of the anionic polymer and the cationic polymer is degraded by enzymes produced by bacteria but not produced by humans.

In some embodiments, the particles of the present invention are core-shell particles. In one embodiment, the core comprises the cationic polymer. In another embodiment, the core comprises the anionic polymer. In one embodiment, the shell comprises the anionic polymer. In another embodiment, the shell comprises the cationic polymer. In one embodiment, the cationic polymer coats the surface of the particles.

In some embodiments, the anionic polymer and the cationic polymer are bound via electrostatic interactions. In one embodiment, the cationic polymer is a crosslinking agent in the anionic polymer matrix. In one embodiment, the anionic polymer and the cationic polymer are not covalently bound. In another embodiment, the anionic polymer and the cationic polymer are covalently bound. In one embodiment, the cationic polymer is covalently bound to the surface the drug delivery particles.

In one embodiment, the ratio of negative charge in the anionic polymer (N) to positive charge in the cationic polymer (P), N:P, is between about 1:1 and about 15:1. In one embodiment, the ratio N:P is about 1:1. In one embodiment, the ratio N:P is about 2.5:1. In one embodiment, the ratio N:P is about 5:1. In one embodiment, the ratio N:P is about 7.5:1. In one embodiment, the ratio N:P is about 10:1. In one embodiment, the ratio N:P is about 12.5:1. In one embodiment, the ratio N:P is about 15:1.

In some embodiments, the size of the particles may change upon exposure to water or to physiologic media. In some embodiments, the particles expand to up to about 3 times their original size in water or physiologic media. In some embodiments, the particles expand up to about 2 times their original size in water or physiologic media. In one embodiment, the size of the swollen particles depends on the N:P ratio of the particles. In some embodiments, the particles of the present invention degrade after a certain time period in physiologic media. In one embodiment, the particles degrade after between 0.5 and 80 hours. In one embodiment, the particles degrade after about 0.5 hours. In one embodiment, the particles degrade after about 4 hours. In one embodiment, the particles degrade after about 20 hours. In one embodiment, the particles degrade after about 50 hours. In one embodiment, the particles degrade after about 70 hours. In one embodiment, the particles degrade after about 80 hours. In one embodiment, the time that it takes the particles to degrade depends on the N:P ratio of the particles.

The biologically active agent can be any biologically active agent that would be appreciated by one of skill in the art. Exemplary bioactive compounds include, but are not limited to, antimicrobial compounds, anti-cancer compounds, antiviral compounds, and monoclonal antibodies or other biologics.

Non-limiting examples of antimicrobial compounds are levofloxacin, aminosalicycic acid, capreomycin, ethambutol, isoniazid, pyrazinamide, rifabutin, rifampin, clofazime, doxycycline, neomycin, clindamycin, minocycline, gentamycin, rifampicin, chlorhexidine, chloroxylenol, methylisothizolone, thymol, α-terpineol, cetylpyridinium chloride, hexachlorophene, triclosan, nitrofurantoin, erythromycin, nafcillin, cefazolin, imipenem, astreonam, gentamicin, sulfamethoxazole, vancomycin, ciprofloxacin, trimethoprim, rifampin, metronidazole, clindamycin, teicoplanin, mupirocin, azithromycin, clarithromycin, ofoxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linexolid, temafloxacin, tosufloxacin, clinafloxacin, sulbactam, clavulanic acid, amphotericin B, fluconazole, itraconazole, ketoconazole, nystatin, penicillins, cephalosporins, carbepenems, betalactams antibiotics, aminoglycosides, macrolides, lincosamides, glycopeptides, tetracylines, chloramphenicol, quinolones, fucidines, sulfonamides, trimethoprims, rifamycins, oxalines, streptogramins, lipopeptides, ketolides, polyenes, azoles, echinocandines, and any combination(s) thereof. In one embodiment, the antimicrobial compound is an antimycobacterial compound. In one embodiment, the composition comprises a multidrug cocktail. In one embodiment, the multidrug cocktail comprises rifampicin, isoniazid, pyrazinamide and ethambutol.

In one embodiment, the antimicrobial compound is an inhibitor of trans-translation or protein synthesis. Exemplary inhibitors include, but are not limited to, kanamycin, gentamicin, hygromycin B, streptomycin, G418, paromomycin, spectinomycin, fusidic acid, thiostrepton, GE2270A, GE37468, erythromycin, spiramycin, tylosin, KKL-10, KKL-22, KKL-35, KKL-52, and KKL-55.

Non-limiting examples of anti-cancer compounds are acivicin; aclarubicin; acodazole hydrochloride; acronine; adozelesin; aldesleukin; altretamine; ambomycin;

ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide;

safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A;

bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; j asplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is doxorubicin.

Exemplary antiviral drugs include, but are not limited to, abacavir, aciclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, entry inhibitors, famciclovir, fomivirsen, fosamprenavir, foscarnet, fosfonet, ganciclovir, ibacitabine, imunovir, idoxuridine, imiquimod, indinavir, inosine, interferon type iii, interferon type ii, interferon type i, interferon, lamivudine, lopinavir, loviride, maraviroc, moroxydine, methisazone, nelfinavir, nevirapine, nexavir, nucleoside analogues, oseltamivir (Tamiflu), peginterferon alfa-2a, penciclovir, peramivir, pleconaril, podophyllotoxin, raltegravir, ribavirin, rimantadine, ritonavir, pyramidine, saquinavir, stavudine, tea tree oil, tenofovir, tenofovir disoproxil, tipranavir, trifluridine, trizivir, tromantadine, truvada, valaciclovir (Valtrex), valganciclovir, vicriviroc, vidarabine, viramidine, zalcitabine, zanamivir (Relenza), and zidovudine.

Exemplary monoclonal antibodies or other biologics include, but are not limited to 3F8, 8H9, Abagovomab, Abciximab, Adalimumab, Adecatumumab, Afelimomab, Afutuzumab, Alacizumab pegol, ALD518, Alemtuzumab, Altumomab pentetate, Amatuximab, Anatumomab mafenatox, Anrukinzumab, Apolizumab, Arcitumomab, Aselizumab, Atinumab, Atlizumab, Atorolimumab, Bapineuzumab, Basiliximab, Bavituximab, Bectumomab, Belimumab, Benralizumab, Bertilimumab, Besilesomab, Bevacizumab, Biciromab, Bivatuzumab mertansine, Blinatumomab, Blosozumab, Brentuximab vedotin, Briakinumab, Brodalumab, Canakinumab, Cantuzumab mertansine, Cantuzumab ravtansine, Caplacizumab, Capromab pendetide, Carlumab, Catumaxomab, CC49, Cedelizumab, Certolizumab pegol, Cetuximab, Citatuzumab bogatox, Cixutumumab, Clazakizumab, Clenoliximab, Clivatuzumab tetraxetan, Conatumumab, Crenezumab, CR6261, Dacetuzumab, Daclizumab, Dalotuzumab, Daratumumab, Denosumab, Detumomab, Dorlimomab aritox, Drozitumab, Ecromeximab, Eculizumab, Edobacomab, Edrecolomab, Efalizumab, Efungumab, Elotuzumab, Elsilimomab, Enavatuzumab, Enlimomab pegol, Enokizumab, Ensituximab, Epitumomab cituxetan, Epratuzumab, Erlizumab, Ertumaxomab, Etaracizumab, Etrolizumab, Exbivirumab, Fanolesomab, Faralimomab, Farletuzumab, FBTA05, Felvizumab, Fezakinumab, Ficlatuzumab, Figitumumab, Flanvotumab, Fontolizumab, Foralumab, Foravirumab, Fresolimumab, Fulranumab, Galiximab, Ganitumab, Gantenerumab, Gavilimomab, Gemtuzumab ozogamicin, Gevokizumab, Girentuximab, Glembatumumab vedotin, Golimumab, Gomiliximab, GS6624, Ibalizumab, Ibritumomab tiuxetan, Icrucumab, Igovomab, Imciromab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lebrikizumab, Lemalesomab, Lerdelimumab, Lexatumumab, Libivirumab, Lintuzumab, Lorvotuzumab mertansine, Lucatumumab, Lumiliximab, Mapatumumab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nerelimomab, Nimotuzumab, Nivolumab, Nofetumomab merpentan, Ocrelizumab, Odulimomab, Ofatumumab, Olaratumab, Olokizumab, Omalizumab, Onartuzumab, Oportuzumab monatox, Oregovomab, Otelixizumab, Oxelumab, Ozoralizumab, Pagibaximab, Palivizumab, Panitumumab, Panobacumab, Pascolizumab, Pateclizumab, Patritumab, Pemtumomab, Pertuzumab, Pexelizumab, Pintumomab, Placulumab, Ponezumab, Priliximab, Pritumumab, PRO 140, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Sevirumab, Sibrotuzumab, Sifalimumab, Siltuximab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Teneliximab, Teplizumab, Teprotumumab, TGN1412, Ticilimumab, Tigatuzumab, TNX-650, Tocilizumab, Toralizumab, Tositumomab, Tralokinumab, Trastuzumab, TRBS07, Tregalizumab, Tremelimumab, Tucotuzumab celmoleukin, Tuvirumab, Ublituximab, Urelumab, Urtoxazumab, Ustekinumab, Vapaliximab, Vatelizumab, Vedolizumab, Veltuzumab, Vepalimomab, Vesencumab, Visilizumab, Volociximab, Votumumab, Zalutumumab, Zanolimumab, Ziralimumab, and Zolimomab aritox.

The particles of the present invention may further comprise at least one excipient. In one embodiment, the excipient is a pharmaceutically acceptable carrier. As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

In one embodiment, the biologically active agent is localized, or essentially localized, in the core of the core-shell particles. In one embodiment, the biologically active agent is localized, or essentially localized, in the shell of the core-shell particles. In one embodiment, the biologically active agent is localized, or essentially localized, in the core and the shell of the core-shell particles. In one embodiment, the biologically active agent is localized, or essentially localized, on the outer surface of the core-shell particles.

In one embodiment, the biologically active agent is not covalently bound to the cationic polymer or to the anionic polymer. In one embodiment, the biologically active agent is covalently bound to the cationic polymer via a tether. In one embodiment, the biologically active agent is covalently bound to the anionic polymer via a tether. In one embodiment, the biologically active agent is covalently bound to both the cationic polymer and the anionic polymer via at least tether. In one embodiment, the tether degrades under physiologic conditions. In one embodiment, the tether comprises at least one of a polypeptide, a polysaccharide, a poly lactic acid, or a polyanhydride.

In one embodiment, the biologically active agent is released under physiological conditions, such as in physiologic media. In one embodiment, the biologically active agent is released at a rate represented by zero-order kinetics. In one embodiment, the biologically active agent is released at a rate represented by first-order kinetics. In one embodiment, the biologically active is retained until the particles degrade. In one embodiment, the release rate of the biologically active agent can be tuned through localization of the agent within the particles, the N:P ratio of the particles, and the presence/absence of additional cationic peptides.

In one embodiment, the particles of the present invention are generally spherical in shape. In one embodiment, the particles of the present invention have a ruffled surface. In another embodiment, the particles have a smooth surface. There is no particular limit to the size of the particles of the present invention. In some embodiments, the particles have diameter between 50 and 5000 nm. In some embodiments, the particles have a diameter between 50 and 200 nm. In one embodiment, the particles have a diameter of about 50 nm. In one embodiment, the particles have a diameter of about 60 nm. In one embodiment, the particles have a diameter of about 80 nm. In one embodiment, the particles have a diameter of about 100 nm. In one embodiment, the particles have a diameter of about 120 nm. In one embodiment, the particles have a diameter of about 140 nm. In one embodiment, the particles have a diameter of about 160 nm. In one embodiment, the particles have a diameter of about 180 nm. In one embodiment, the particles have a diameter of about 200 nm. In some embodiments, the particles have a diameter between 500 and 5000 nm. In one embodiment, the particles have a diameter between 1000 and 3000 nm. In one embodiment, the particles have a diameter of about 200 nm. In one embodiment, the particles have a diameter of about 500 nm. In one embodiment, the particles have a diameter of about 750 nm. In one embodiment, the particles have a diameter of about 1000 nm. In one embodiment, the particles have a diameter of about 1250 nm. In one embodiment, the particles have a diameter of about 1500 nm. In one embodiment, the particles have a diameter of about 1750 nm. In one embodiment, the particles have a diameter of about 2000 nm. In one embodiment, the particles have a diameter of about 2250 nm. In one embodiment, the particles have a diameter of about 2500 nm. In one embodiment, the particles have a diameter of about 2750 nm. In one embodiment, the particles have a diameter of about 3000 nm.

In some embodiments, the outer surface of the particles exhibits a negative charge. In other embodiments, the outer surface of the particles exhibits a positive charge. In other embodiments, the outer surface of the particles is neutral. In one embodiment, the charge of the outer surface of the particles can be measured by its zeta potential. In one embodiment, the zeta potential of the particles is between −50 and 50 mV. In one embodiment, the zeta potential of the particles is between −50 and 30 mV. In one embodiment, the zeta potential of the particles is about −50 mV. In one embodiment, the zeta potential of the particles is about −40 mV. In one embodiment, the zeta potential of the particles is about −30 mV. In one embodiment, the zeta potential of the particles is about −20 mV. In one embodiment, the zeta potential of the particles is about −10 mV. In one embodiment, the zeta potential of the particles is about 0 mV. In one embodiment, the zeta potential of the particles is about 10 mV. In one embodiment, the zeta potential of the particles is about 20 mV. In one embodiment, the zeta potential of the particles is about 30 mV.

Methods of Making

In one aspect, the present invention relates to a method of forming a plurality of drug delivery particles. An exemplary method is provided in FIG. 100. In step 110, a sample solution comprising at least one anionic polymer is provided. In step 120, a bath solution comprising at least one cationic polymer is provided. In step 130, the sample solution is electrosprayed into the bath solution to form a drug delivery particle solution. In step 140, the drug delivery particles are isolated from the drug delivery particle solution. At least one of the sample solution, the bath solution, or the solution of drug delivery particles further comprises at least one biologically active agent.

Electrospraying is a technique in which a voltage is applied to the sample solution as it is passed through a capillary tip; coulombic repulsion within the ejected solution generates a fine mist that is collected in the bath solution. In some embodiments, the voltage applied to the sample solution is between 1 and 100 kV. In one embodiment, the voltage applied to the sample solution is between 10 and 50 kV. In one embodiment, the voltage applied to the sample solution is about 10 kV. In one embodiment, the voltage applied to the sample solution is about 15 kV. In one embodiment, the voltage applied to the sample solution is about 20 kV. In one embodiment, the voltage applied to the sample solution is about 25 kV. In one embodiment, the voltage applied to the sample solution is about 30 kV. In one embodiment, the voltage applied to the sample solution is about 35 kV. In one embodiment, the voltage applied to the sample solution is about 40 kV. In one embodiment, the voltage applied to the sample solution is about 45 kV. In one embodiment, the voltage applied to the sample solution is about 50 kV.

In one embodiment, the spray rate of the sample solution into the bath solution is between about 0.05 mL/min and about 1 mL/min. In one embodiment, the spray rate of the sample solution into the bath solution is about 0.1 mL/min.

The sample solution can comprise any anionic polymer, including, but not limited to, anionic polymers disclosed herein. In one embodiment, the sample solution comprises between about 0.1 wt % anionic polymer and about 4 wt % anionic polymer. In one embodiment, the sample solution comprises about 0.1 wt % anionic polymer. In one embodiment, the sample solution comprises about 0.2 wt % anionic polymer. In one embodiment, the sample solution comprises about 0.3 wt % anionic polymer. In one embodiment, the sample solution comprises about 0.4 wt % anionic polymer. In one embodiment, the sample solution comprises about 0.5 wt % anionic polymer. In one embodiment, the sample solution comprises about 0.6 wt % anionic polymer. In one embodiment, the sample solution comprises about 0.7 wt % anionic polymer. In one embodiment, the sample solution comprises about 0.8 wt % anionic polymer. In one embodiment, the sample solution comprises about 0.9 wt % anionic polymer. In one embodiment, the sample solution comprises about 1.0 wt % anionic polymer. In one embodiment, the sample solution comprises about 1.5 wt % anionic polymer. In one embodiment, the sample solution comprises about 2.0 wt % anionic polymer. In one embodiment, the sample solution comprises about 2.5 wt % anionic polymer. In one embodiment, the sample solution comprises about 3.0 wt % anionic polymer. In one embodiment, the sample solution comprises about 3.5 wt % anionic polymer. In one embodiment, the sample solution comprises about 4.0 wt % anionic polymer.

The bath solution can comprise any cationic polymer, including, but not limited to, cationic polymers disclosed herein. In one embodiment, the concentration of the bath solution comprising the cationic polymer is between 0.001% and 0.1% w/v. In one embodiment, the concentration to the bath solution is between 0.01% and 0.1% w/v. In one embodiment, the concentration of the bath solution is about 0.01% w/v. In one embodiment, the concentration of the bath solution is between 0.5 and 3 mg/mL. In one embodiment, the concentration of the bath solution is about 1 mg/mL.

In one embodiment, any of the bath solution, sample solution, or drug delivery particle solution further comprises up to about 5% v/v DMSO. In one embodiment, any of the bath solution, sample solution, or drug delivery particle solution further comprises a pharmaceutically acceptable carrier as described elsewhere herein.

In one embodiment, the step of electrospraying the sample solution into the bath solution to form a drug delivery particle solution further comprises the step of incubating the drug delivery solution for at least one hour at least 37° C.

In one embodiment, the step of isolating a plurality of drug delivery particles from the drug delivery particle solution comprises the step of centrifuging the drug delivery particle solution and removing the supernatant. In one embodiment, centrifugation may generate particles of size between about 50 nm and about 300 nm. In one embodiment, the step of isolating a plurality of drug delivery particles from the drug delivery particle solution comprises the step of dialyzing the particles from the drug delivery particle solution. In one embodiment, dialysis may generate larger particles than centrifugation. In one embodiment, dialysis may generate particles of size between about 300 nm and about 1000 nm. In one embodiment, the step of isolating a plurality of drug delivery particles from the drug delivery particle solution comprises the step of filtering the drug delivery particle solution. In one embodiment, the step of isolating a plurality of drug delivery particles from the drug delivery particle solution further comprises the step of lyophilizing the drug delivery particles to form a dry powder.

Methods of Treatment

In one aspect, the present invention relates to a method of treating a mycobacterial infection in a subject in need thereof, the method comprising the step of administering to the subject a formulation comprising the drug delivery particles of the present invention. In one embodiment, administration of a formulation comprising the drug delivery particles of the present invention prior to exposure to mycobacteria can prevent infection.

In one embodiment, the particles of the present invention are prepared as dry powder formulation. In one embodiment, dry powder is suitable for inhalation formulation. In one embodiment, the dry powder formulation comprises particles with a mass median aerodynamic diameter (MMAD) between about 1 and about 5 μm. In one embodiment, the dry powder formulation comprises particles with an MMAD of about 1.5 μm. In one embodiment, the dry powder formulation comprises particles having a negative surface charge, as discussed elsewhere herein.

Pharmaceutical Compositions

Also provided herein are pharmaceutical compositions comprising drug delivery particles of the present invention. The pharmaceutical compositions may be suitable for a variety of modes of administration described herein, including for example systemic or localized administration. The pharmaceutical compositions can be in the form of eye drops, injectable solutions, or in a form suitable for inhalation (either through the mouth or the nose) or oral administration. The pharmaceutical compositions described herein can be packaged in single unit dosages or in multidosage forms.

In some embodiments, the pharmaceutical compositions comprise a pharmaceutically acceptable carrier suitable for administration to human. In some embodiments, the pharmaceutical compositions comprise a pharmaceutically acceptable carrier suitable for intraocular injection. In some embodiments, the pharmaceutical compositions comprise a pharmaceutically acceptable carrier suitable for topical application. In some embodiments, the pharmaceutical compositions comprise a pharmaceutically acceptable carrier suitable for intravenous injection. In some embodiments, the pharmaceutical compositions comprise and a pharmaceutically acceptable carrier suitable for injection into the arteries.

The compositions are generally formulated as sterile, substantially isotonic, and in full compliance with all Good Manufacturing Practice (GMP) regulations of the U.S. Food and Drug Administration. In some embodiments, the composition is free of pathogen. For injection, the pharmaceutical composition can be in the form of liquid solutions, for example in physiologically compatible buffers such as Hank's solution or Ringer's solution. In addition, the drug delivery particle pharmaceutical composition can be in a solid form and redissolved or suspended immediately prior to use. Lyophilized compositions are also included.

For oral administration, the pharmaceutical compositions can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

The present invention in some embodiments provides compositions comprising drug delivery particles and a pharmaceutically acceptable carrier suitable for administration to the eye. Such pharmaceutical carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. Suitable pharmaceutical excipients include starch, glucose, lactose, sucrose, gelatin, malt, rice, sodium state, glycerol monostearate, glycerol, propylene, water, and the like. The pharmaceutical composition, if desired, can also contain minor amounts of wetting or emulsifying agents, or pH buffering agents. The drug delivery particles and other components of the composition may be encased in polymers or fibrin glues to provide controlled release of the molecule. These compositions can take the form of solutions, suspensions, emulsions, ointment, gel, or other solid or semisolid compositions, and the like. The compositions typically have a pH in the range of 4.5 to 8.0. The compositions must also be formulated to have osmotic values that are compatible with the aqueous humor of the eye and ophthalmic tissues. Such osmotic values will generally be in the range of from about 200 to about 400 milliosmoles per kilogram of water ("mOsm/kg"), but will preferably be about 300 mOsm/kg.

In some embodiments, the composition is formulated in accordance with routine procedures as a pharmaceutical composition adapted for injection intravenously, intraperitoneally, or intravitreally. Typically, compositions for injection are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions may further comprise additional ingredients, for example preservatives, buffers, tonicity agents, antioxidants and stabilizers, nonionic wetting or clarifying agents, viscosity-increasing agents, and the like.

Suitable preservatives for use in a solution include polyquaternium-1, benzalkonium chloride, thimerosal, chlorobutanol, methyl paraben, propyl paraben, phenylethyl alcohol, edetate disodium, sorbic acid, benzethonium chloride, and the like. Typically (but not necessarily), such preservatives are employed at a level of from 0.001% to 1.0% by weight.

Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5.

Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%.

Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose and the like.

The use of viscosity enhancing agents to provide topical compositions with viscosities greater than the viscosity of simple aqueous solutions may be desirable. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents know to those skilled in the art. Such agents are typically employed at a level of from 0.01% to 2% by weight.

In some embodiments, there is provided a pharmaceutical composition for delivery of a nucleotide encapsulated in a drug delivery particle. The pharmaceutical composition for gene therapy can be in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical composition can comprise one or more cells which produce the gene delivery system.

In clinical settings, a gene delivery system for a gene therapeutic can be introduced into a subject by any of a number of methods. For instance, a pharmaceutical composition of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter, See U.S. Pat. No. 5,328,470, or by stereotactic injection, Chen et al. (1994), Proc. Natl. Acad. Sci., USA 91: 3054-3057.

Administration

The compositions described herein can be administered to an individual via any route, including, but not limited to, intravenous (e.g., by infusion pumps), intraperitoneal, intraocular, intra-arterial, intrapulmonary, oral, intravesicular, intramuscular, intra-tracheal, subcutaneous, intrathecal, transdermal, transpleural, topical, inhalational (e.g., as mists of sprays dry powders, or aerosols), mucosal (such as via nasal mucosa), gastrointestinal, intraarticular, intracisternal, intraventricular, rectal (i.e., via suppository), vaginal (i.e., via pessary), intracranial, intraurethral, intrahepatic, and intratumoral. In some embodiments, the compositions are administered systemically (for example by intravenous injection). In some embodiments, the compositions are administered locally (for example by intraarterial or intraocular injection). In some embodiments, the compositions are administered by ex vivo incubation or perfusion.

Dosing

The optimal effective amount of the compositions can be determined empirically and will depend on the type and severity of the disease, route of administration, disease progression and health, mass and body area of the individual. Such determinations are within the skill of one in the art. The effective amount can also be determined based on in vitro complement activation assays. Examples of dosages of drug delivery particles which can be used for methods described herein include, but are not limited to, an effective amount within the dosage range of any of about 0.01 mg/kg to about 300 mg/kg, or within about 0.1 mg/kg to about 40 mg/kg, or with about 1 mg/kg to about 20 mg/kg, or within about 1 mg/kg to about 10 mg/kg. In some embodiments, the amount of biologically active agent administered to an individual is about 10 mg to about 500 mg per dose, including for example any of about 10 mg to about 50 mg, about 50 mg to about 100 mg, about 100 mg to about 200 mg, about 200 mg to about 300 mg, about 300 mg to about 500 mg, about 500 mg to about 1 mg, about 1 mg to about 10 mg, about 10 mg to about 50 mg, about 50 mg to about 100 mg, about 100 mg to about 200 mg, about 200 mg to about 300 mg, about 300 mg to about 400 mg, or about 400 mg to about 500 mg per dose.

The compositions comprising drug delivery particles may be administered in a single daily dose, or the total daily dose may be administered in divided dosages of two, three, or four times daily. The compositions can also be administered less frequently than daily, for example, six times a week, five times a week, four times a week, three times a week, twice a week, once a week, once every two weeks, once every three weeks, once a month, once every two months, once every three months, or once every six months. The compositions may also be administered in a sustained release formulation, such as in an implant which gradually releases the composition for use over a period of time, and which allows for the composition to be administered less frequently, such as once a month, once every 2-6 months, once every year, or even a single administration. The drug delivery particles may be administered by injection or surgical implantation in various locations.

Dosage amounts and frequency will vary according the particular formulation, the dosage form, and individual patient characteristics. Generally speaking, determining the dosage amount and frequency for a particular formulation, dosage form, and individual patient characteristic can be accomplished using conventional dosing studies, coupled with appropriate diagnostics.

Combination Therapy

In some embodiments, provided pharmaceutical formulations are administered to a subject in combination with one or more other therapeutic agents or modalities, for example, useful in the treatment of one or more diseases, disorders, or conditions treated by the relevant provided pharmaceutical formulation, so the subject is simultaneously exposed to both.

The particular combination of therapies (substances and/or procedures) to employ in a combination regimen will take into account compatibility of the desired substances and/or procedures and the desired therapeutic effect to be achieved. In some embodiments, provided compositions can be administered concurrently with, prior to, or subsequent to, one or more other therapeutic agents (e.g., desired known antimycobacterial therapeutics).

It will be appreciated that the therapies employed may achieve a desired effect for the same disorder (for example, a therapeutic compound useful for mycobacterial infections administered concurrently with a composition of the present invention), or they may achieve different effects (for example, a composition of the present invention may be administered concurrently with a therapeutic agent that is useful for alleviating adverse side effects, for instance, fever, pain, nausea, etc.). In some embodiments, the composition of the present invention are administered with a second therapeutic agent.

As used herein, the terms "in combination with" and "in conjunction with" mean that the drug delivery particles of the present invention can be administered concurrently with, prior to, or subsequent to, one or more other desired therapeutics such as an analgesic, antibacterial, antiviral, anticancer, or biologic agent including but not limited to a sub-therapeutic dose of such an agent. In general, each substance will be administered at a dose and/or on a time schedule determined for that agent.

In certain embodiments, the method comprises administering a composition comprising a combination of an antibacterial agent and the drug delivery particles described herein.

In certain embodiments, the method comprises administering one or more compositions. For example, in one embodiment, the method comprises administering a first composition comprising an antibacterial agent and a second composition comprising the drug delivery particles described herein. The different compositions may be administered to the subject in any order and in any suitable interval. For example, in certain embodiments, the one or more compositions are administered simultaneously or near simultaneously. In certain embodiments, the method comprises a staggered administration of the one or more compositions, where a first composition is administered and a second composition administered at some later time point. Any suitable interval of administration which produces the desired therapeutic effect may be used.

In certain embodiments, the method has an additive effect, wherein the overall effect of the administering a combination of therapeutic agents or procedures is approximately equal to the sum of the effects of administering each therapeutic agent or procedure alone. In other embodiments, the method has a synergistic effect, wherein the overall effect of administering a combination of therapeutic agents or procedures is greater than the sum of the effects of administering each therapeutic agent or procedure alone.

Unit Dosages, Articles of Manufacture, and Kits

Also provided are unit dosage forms of drug delivery particle compositions, each dosage containing from about 0.01 mg to about 50 mg, including for example any of about 0.1 mg to about 50 mg, about 1 mg to about 50 mg, about 5 mg to about 40 mg, about 10 mg to about 20 mg, or about 15 mg of the biologically active agent. In some embodiments, the unit dosage forms of drug delivery particles comprise about any of 0.01 mg-0.1 mg, 0.1 mg-0.2 mg, 0.2 mg-0.25 mg, 0.25 mg-0.3 mg, 0.3 mg-0.35 mg, 0.35 mg-0.4 mg, 0.4 mg-0.5 mg, 0.5 mg-1.0 mg, 10 mg-20 mg, 20 mg-50 mg, 50 mg-80 mg, 80 mg-100 mg, 100 mg-150 mg, 150 mg-200 mg, 200 mg-250 mg, 250 mg-300 mg, 300 mg-400 mg, or 400 mg-500 mg biologically active agent. The term "unit dosage form" refers to a physically discrete unit suitable as unitary dosages for an individual, each unit containing a predetermined quantity of active material calculated to produce the desired therapeutic effect, in association with a suitable pharmaceutical carrier, diluent, or excipient. These unit dosage forms can be stored in suitable packaging in single or multiple unit dosages and may also be further sterilized and sealed.

The present invention also provides kits comprising compositions (or unit dosages forms and/or articles of manufacture) described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing any methods described herein.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

Example 1: Inhalable Antimicrobials

Figure 2:
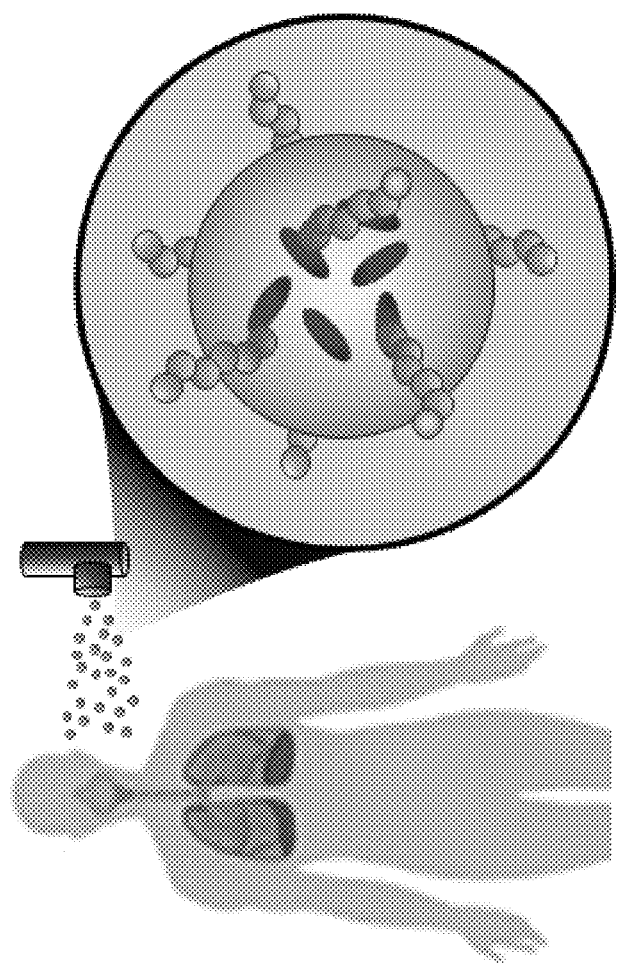
FIG. 2 depicts the delivery of an exemplary anti-TB microgel composition to the lungs. Positively charged AMPs (orange) are complexed with FDA approved hyaluronic acid (grey) to form biodegradable microgels in high yield and low cost. Antibiotics loaded into the particle is a plot of cell viability; the novel trans-translation inhibitor KKL-35 was added at indicated concentrations to cultures of MTb and cell viability measured via plating assays.

A new class of inhalable microparticle gels ('microgels') formed from the electrostatic cross-linking of hyaluronic acid (HA), an FDA approved anionic polysaccharide (Monheit and Coleman, Dermatol. Ther. 2006, 19 (3), 141-150), and cationic antimycobacterial peptides (AMPs) (FIG. 2). The premise of this strategy lies in exploiting the ability of AMPs to elicit rapid and potent lytic destruction of drug-sensitive and -resistant MTb (Ramón-Garcia, et al., Antimicrob. Agents Chemother. 2013, 57 (5), 2295-2303), while minimizing their off-target toxicity via local aerosol delivery to infected lung tissue. These cationic peptides elicit their activity by preferentially binding to anionic motifs on the microbe surface and inserting themselves into the bacterial membrane to form a peptide-lipid complex (Gutsmann, Biochim. Biophys. Acta, Biomembr. 2016, 1858 (5), 1034-1043; Zasloff, Nature 2002, 415 (6870), 389-395). This perturbation leads to thinning and altered curvature of the microbial membrane ultimately resulting in pore formation and bacterial lysis. This mechanism is distinct from conventional antibiotics that target intracellular pathways involved in bacterial metabolism and replication, and thus AMPs are effective towards drug-resistant MTb. Similarly, the ability of AMPs to disrupt the bacterial cell wall makes them equally as potent towards mycobacteria in a non-proliferative state as they are towards replicating cells.

To compliment this acute activity, degradation of the HA microgel matrix by bacterially secreted enzymes affords long-term release of encapsulated antibiotics directly to infected lung tissue. In parallel, phagocytic uptake of drug-loaded microgels by lung macrophages allows for clearance of pathogens protected within these infected host cells and associated granulomas. Collectively, this approach affords direct delivery of AMPs and antibiotics to infected lung tissue to elicit rapid and potent killing of MDR- and XDR-TB with minimal side effects, while controllably releasing encapsulated drug to provide durable anti-TB responses with reduced dosing frequency compared to conventional oral regimens.

Unique to this approach is the ability to synthesize microgels via electrostatic cross-linking of AMPs, which are active towards drug-resistant bacteria, and biocompatible carbohydrates. This eliminates the need for harsh chemicals and cross-linking reagents during synthesis, and yields a biomaterial that is inherently antimicrobial and likely biocompatible. Further, in addition to their potential to kill MDR- and XDR-TB, AMPs have a number of other unique properties rarely enjoyed by traditional small molecule antibiotics. First, it is generally regarded that, due to their rapid and membrane-specific mechanisms of action, bacterial resistance towards AMPs is unlikely (Abedinzadeh, et al., J. Antimicrob. Chemother. 2015, 70 (5), 1285-1289). Secondly, permeabilization of bacterial membranes by AMPs can enhance the uptake of delivered drugs, thereby increasing their potency. Finally, most AMPs are short sequences that, due to advances in microwave synthesis (Collins, et al., Organic Letters 2014, 16 (3), 940-943), can be prepared quickly, at low cost and in high yield and purity.

It is worth noting that formulation of AMPs into a particulate carrier is ideally suited for their aerosol delivery to the lung. The cationic nature of AMPs can lead to their adsorption to upper airway mucosal membranes and thus prevent distribution to infected lower bronchial and alveolar tissue, if not formulated into a micron-sized carrier (Cryan, AAPS J. 2005, 7 (1), E20-E41). Further, encapsulating AMPs within the microgel matrix serves to inhibit their recognition and destruction by proteases present in the inflammatory diseased lung (Lange, et al., J. Pharm. Sci. 2001, 90 (10), 1647-1657), and minimizes their off-target distribution and toxicity towards healthy epithelial tissue and immune cells.

Figure 3:
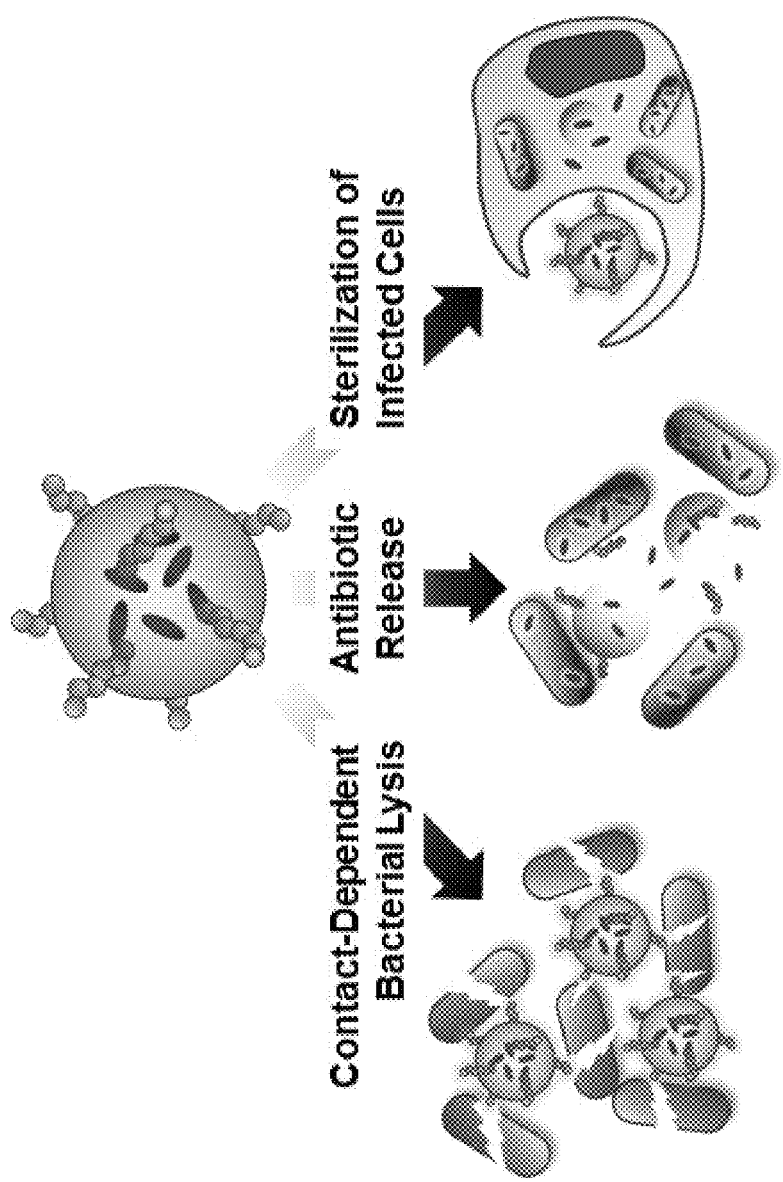

The anionic HA component of microgels also imparts a number of distinct advantages over traditional particles. Hyaluronidases, the group of enzymes responsible for HA degradation, are actively secreted by MTb in an effort to utilize HA from the host's extracellular matrix as a carbon source (Hirayama, et al., PLoS Pathog. 2009, 5 (10), e1000643). This suggests that particle degradation and drug release will occur preferentially to MTb microbes, thereby increasing the effectiveness of delivered antibiotics and minimizing their off-target effects. Further, by modulating the molecular weight of HA in the particle matrix allows for tuning of the enzymatic degradation of the particles and thus controls the rate of antibiotic release; a property difficult to recapitulate with standard synthetic polymers. Together, this allows for therapeutic concentrations of the drug to persist at the disease site for long periods of time and provide lasting anti-TB therapy. In addition to its influence on drug release, binding of HA by CD44 receptors expressed on the surface of macrophages leads to rapid and efficient uptake of drug-loaded microgels into infected immune cells (Aruffo, et al., Cell 1990, 61 (7), 1303-1313; Kamat, et al., Bioconj. Chem. 2010, 21 (11), 2128-2135). Degradation of the particles within the macrophage phagolysosome, which also contains hyaluronidases (Goggins, et al., J. Histochem. Cytochem. 1968, 16 (11), 688-692), ultimately allows for intracellular release of loaded AMPs and antibiotics to clear MTb protected within these infected cellular hosts. Additionally, incorporation of these 'carrier' macrophages into granulomas permits delivery of AMPs and antibiotics to MTb protected within this niche environment (FIG. 3).

In addition to standard TB antibiotics, the present invention relates to the delivery of a new class of recently-discovered anti-TB drug candidates that inhibit the trans-translation pathway to kill both growing MTb and non-replicating persister cells (Ramadoss, et al., Proc. Nat. Acad. Sci. U.S.A. 2013, 110 (25), 10282-10287). This pathway is a good target for antibiotic development as it is required for MTb growth (Keiler, Nat. Rev. Micro. 2015, 13 (5), 285-297), is not present in animals so specific inhibitors may not have side effects, and it has not been targeted for drug development in the past. However, these compounds are limited by poor aqueous solubility and thus serve as ideal candidates to demonstrate the ability of microgels to improve drug formulation and delivery.

In summation, drug-loaded AMP microgels represent a transformative tool for TB therapy with potential to elicit potent antimycobacterial activity towards drug-resistant MTb, in both the replicative and latent state, while employing an extended drug release strategy to minimize dosing frequency for TB patient.

Materials and Methods

Figure 4:
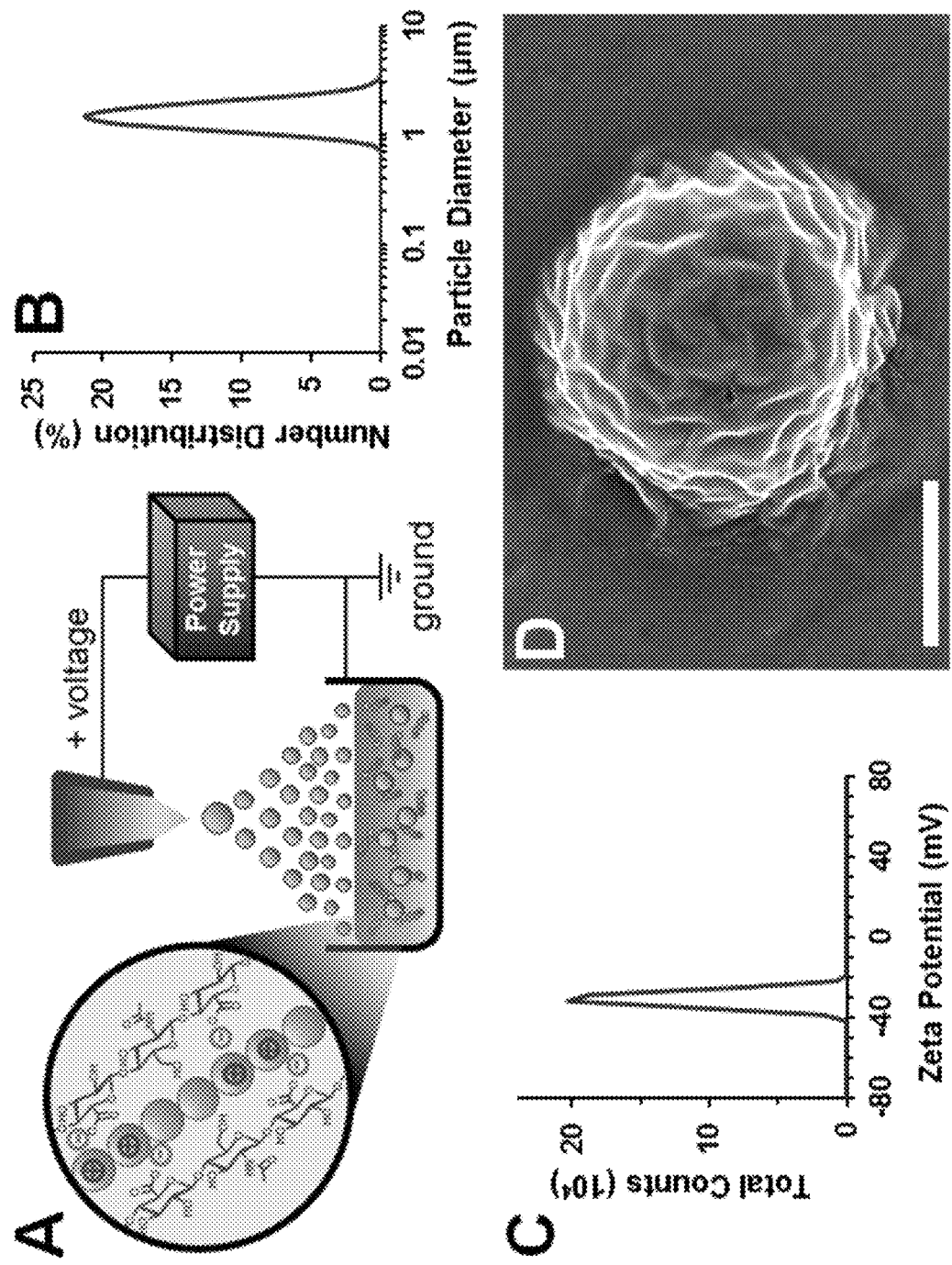
Figure 6:
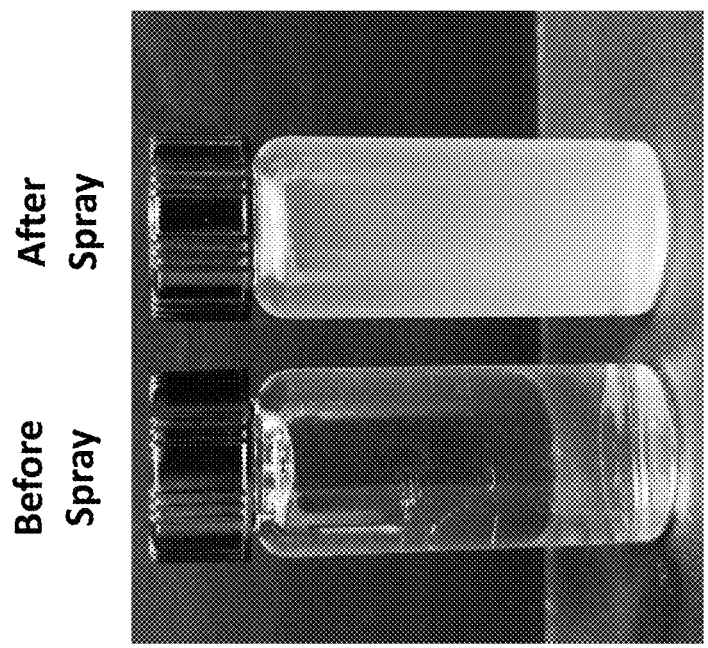
FIG. 6 is a photograph showing exemplary microgels prepared using the methods of the present invention.

An electrospray synthesis process has been developed that affords rapid and high-yielding production of AMP microgels (FIG. 4A; FIG. 6). Antimicrobial peptides having activity against mycobacteria, in addition to other bacterial strains, were identified. These peptides are given in Tables 1, 2, and 3. Though the experimental AMPs have C-terminal amido groups due to chemical synthesis, it is unlikely that the C-terminal amido group has a pronounced effect on the antimycobacterial effect of the peptides. AMPs terminated with a free carboxylate or with some other functionality will likely retain their antimycobacterial properties. Microgels are prepared by spraying a 2 wt % solution of HA (100 kDa) into an aqueous bath containing 1 mg/mL of a cationic AMP with potent anti-MTb activity. Peptides were synthesized and purified using standard solid-phase techniques, with purity >95% as indicated by LC-MS. Importantly, this synthetic approach produced gram quantities of the particles, referred to as TB1 microgels, in <1 hour and at low cost (<$50/gram). Following purification, dynamic light scattering indicated TB1 particles are approximately 1.5 µm in diameter (FIG. 4B). Although no consensus has been reached, it is generally regarded that inhalable microparticles 1-5 µm in size are ideally suited to distribute to the lower respiratory tract and alveolar epithelium, due to airflow convection and gravitational effects (Kleinstreuer, et al., Annu. Rev. Biomed. Eng. 2008, 10, 195-220), while still being readily phagocytosed by alveolar macrophages (Lawlor, et al., Mol. Pharmaceutics 2011, 8 (4), 1100-1112). Importantly, these particles have a negative surface charge (FIG. 4C), suggesting they should not be prematurely adsorbed to the upper airway during inhalation. Electron microscopy reveals an usual 'ruffled' surface morphology of the particles (FIG. 4D), which suggests a large surface area available to engage bacterial pathogens and elicit contact-dependent lysis.

TABLE 1

Exemplary AMP sequences with anti-MTb activity.

| Entry | Sequence[a] | Formal Charge[b] | $IC_{90}$ (µM)[c] M. tuberculosis | $IC_{90}$ (µM)[c] M. smegmatis | $SI_{90}$[d] |
|---|---|---|---|---|---|
| 1 | WKWLKKWIK-$NH_2$ (SEQ ID NO: 55) | +5 | 1.1 | 1.9 | 21.3 |
| 2 | ILRWKWRWWRWRR-$NH_2$ (SEQ ID NO: 51) | +7 | 2.4 | 2.4 | 21.3 |
| 3 | KRWWKWWRR-$NH_2$ (SEQ ID NO: 53) | +6 | 3.1 | 4.9 | 51.2 |
| 4 | RRWWRWVVW-$NH_2$ (SEQ ID NO: 54) | +4 | 5.6 | 11.4 | 32.0 |
| 5 | KRWHWWRRHWVVW-$NH_2$ (SEQ ID NO: 52) | +7 | see Table 3 | | N/D[e] |

[a]All sequences are prepared synthetically with amidated C-terminus.; [b]Peptide formal charge including the N-terminal amine.; [c]Minimum concentration inhibiting 90% culture growth.; [d]Selectivity index at $IC_{90}$ against the THP-1 human macrophage control cell line; [e]N/D = not determined

TABLE 2

AMPs, number of AA residues, and formal charges

| | Sequence | # AA | Formal Charge |
|---|---|---|---|
| $AMP_1$ | WKWLKKWIK-$NH_2$ (SEQ ID NO: 55) | 9 | +5 |
| $AMP_2$ | KRWWKWWRR-$NH_2$ (SEQ ID NO: 53) | 9 | +6 |
| $AMP_3$ | RRWWRWVVW-$NH_2$ (SEQ ID NO: 54) | 9 | +4 |
| SMAS-1 | KRWHWWRRHWVVW-$NH_2$ (SEQ ID NO: 52) | 13 | +7 |

TABLE 3

MIC values for AMPs listed in Table 2.

| Gram | Strain | MIC (µM) | | | |
|---|---|---|---|---|---|
| | | AMP$_1$ | AMP$_2$ | AMP$_3$ | SMAS-1 |
| + | MR *S. aureus* | >80 | 80 | 20 | >80 |
| + | MS *S. aureus* | >80 | 80 | 20 | >80 |
| + | *B. anthrax* | 10 | 80 | 20 | >80 |
| − | *P. aeruginosa* | 10 | 20 | 80 | 50 |
| − | *A. baumannii* | 25 | 80 | 10 | 50 |
| − | *S. enterica* | 40 | 80 | 80 | 80 |
| − | *H. influenzae* | 80 | 80 | 40 | 80 |
| +/− | *M. smegmatis* | 20 | 20 | 20 | 5 |
| +/− | *M. tuberculosis* | 20 | 10 | 20 | 3 |

Three additional microgel formulations prepared using AMPs with varied composition, formal charge and hydrophobicity are synthesized and their antibacterial activity tested. (Table 1, Entries 2-4). Thus, the flexibility of the electrospray synthetic approach is tested, the physiochemical properties of the peptide cross-linker that affords competent microgels is identified, and a small library of particles with which to screen for anti-MTb activity and specificity is provided. AMPs are synthesized and purified using known methods and instrumentation (Medina, et al., Biomaterials 2015, 53, 545-553; Medina, and Schneider, J. Controlled Release 2015, 209, 317-326; Smith, et al., Nat. Nano. 2016, 11 (1), 95-102; Medina, et al., Angew. Chem. Int. Ed. 2016, 55 (10), 3369-3372; Ishikawa, et al., Cell Chem. Biol. 2017, 24 (2), 149-158). Peptides are used at >95% purity (as assessed by LC-MS). Like Table 1, the AMPs listed in Table 2 display potent lytic activity towards MTb, as indicated by low micromolar IC$_{90}$ (inhibitory concentration of 90% culture growth) values (Ramón-Garcia, et al., Antimicrob. Agents Chemother. 2013, 57 (5), 2295-2303), and *M. smegmatis*, a non-pathogenic strain used as a model for MTb. Importantly, these sequences are ~20-50 times more selective in their lytic action towards MTb over a human macrophage control cell line (expressed as selectivity index, SI, in Table 1). This is significant as many antibacterial peptides have narrow therapeutic indexes, and can cause membrane disruption and necrosis of healthy mammalian cells at elevated concentrations (Fjell, et al., Nat. Rev. Drug Discov. 2012, 11 (1), 37-51). This suggests that microgels prepared from these AMPs are capable of eliciting potent antibacterial activity with minimal off-target effects.

Using optimized electrospray conditions (24 kV, 2 wt % of 100 kDa HA), the ability of these AMPs to form competent microgels at bath concentrations of 0.5-3 mg/mL of the peptide is screened. Following purification by dialysis and lyophilization, the size and surface charge of the particles is measured by dynamic light scattering and zeta potential analysis, respectively. Scanning electron microscopy is performed on select formulations to confirm particle size and visualize surface topography. Formulations that afford 1-5 µm particles, and which possess a neutral or negative surface charge, are tested for antimycobacterial activity and specificity against healthy human control cell lines.

Figure 7:
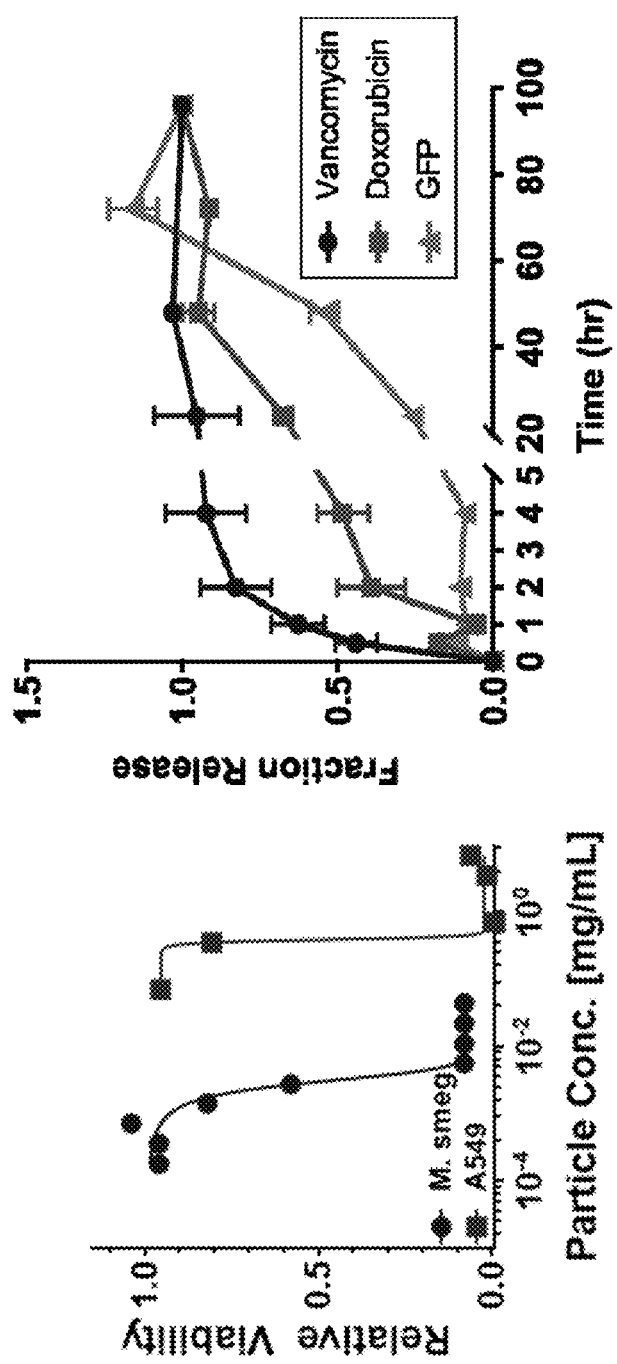
FIG. 7, comprising FIGS. 7A and 7B, demonstrates the biocompatibility and bioavailability of exemplary antimicrobial compositions.
Figure 8:
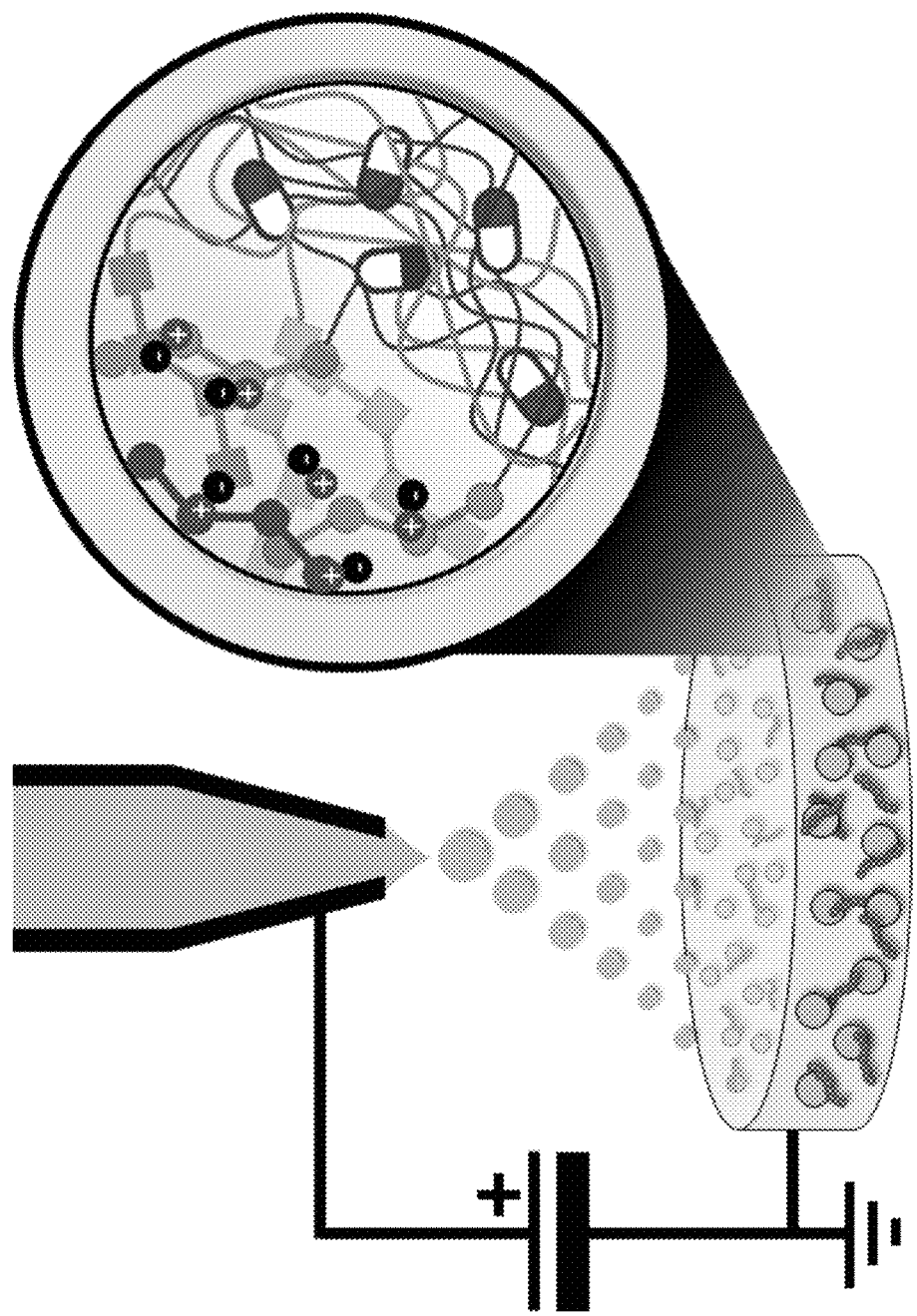
FIG. 8 depicts the production of exemplary drug delivery particles by electrospray ionization. An aqueous solution of anionic HA (orange) is infused through an electrically-charged capillary, causing it to spray as nano-scale droplets. Contact of HA nanodroplets with ε-poly-L-lysine (PLL; purple) in the bath solution leads to electrostatic assembly of nanogel particles. Therapeutic agents or biochemical sensors (green/white) present during nanogel assembly become physically entrapped within the particle network.

For growth inhibition studies, non-virulent MTb (H37Ra) and *M. smegmatis* are incubated with 0.001-10 mg/mL TB1-TB4 microgels for 24-72 hours (FIG. 7). At specific time points, antibacterial activity is evaluated by measuring bacterial load via optical density (OD600) of microgel-treated samples relative to untreated cultures or those lysed with Triton X-100 as negative and positive controls, respectively. In separate experiments, MTb cells are incubated for 24 hours with select microgels at their IC$_{90}$, and scanning electron microscopy is performed to visualize membrane disruption. The non-specific toxicity of selected formulations is tested as a function of particle concentration towards human THP-1 macrophages and A549 epithelial cells as controls. THP-1 is a human monocyte line that differentiates into macrophages upon treatment with phorbol 12-myristate 13-acetate (PMA) (Auwerx, Experientia 1991, 47 (1), 22-31). A549 is a lung cancer cell line that has been previously used as a surrogate for pulmonary epithelium (Crabbé, et al., Sci. Rep. 2017, 7, 43321; Carterson, et al., Infection and Immunity 2005, 73 (2), 1129-1140). Selectivity indices of the formulations, calculated as IC$_{90(control)}$/IC$_{90(MTb)}$, is determined for each control cell line and candidate microgels with SI's≥20 are chosen for further study.

In separate experiments, fluorescent confocal microscopy is used to directly observe binding of selected microgel formulations to the surface of MTb and evaluate contact-dependent lysis. Fluorescently-labeled AMPs are prepared using previously developed protocols (Medina, and Schneider, J. Controlled Release 2015, 209, 317-326; Medina, et al., Angew. Chem. Int. Ed. 2016, 55 (10), 3369-3372), the labeled peptides (10-50 µg/mL) are doped into the electrospray bath solution containing unlabeled AMPs. The resulting fluorescent microgels are incubated with H37Ra MTb at their IC$_{90}$ for 0.5-12 hours, followed by counterstaining treated cells with DAPI to visualize and propidium iodide (PI) to indicate membrane disruption. These experiments allow for the visual determination of the relative contribution of direct contact-dependent lysis, as indicated by co-localization of fluorescent particles and PI positive cells, or loss of particle integrity leading to release of free AMPs to MTb cells, on the overall antibacterial activity of selected microgels.

The formulation of AMP microgels is optimized to afford micron-sized particles with potent anti-TB activity and minimal off-target toxicity. Formulations that meet the SI≥20 criteria are advanced for drug loading and release assays. The preliminary formulation conditions afford particles within a size range of 1-5 µm. Confirmation that AMPs are displayed at the microgel surface is determined by performing confocal microscopy on fluorescent formulations. In some cases, the HA matrix is partially cross-linked using polylysine, a commercially available biocompatible polycation. Polylysine limits the diffusion of AMPS into the particle core and thus promotes their preferential display at the surface. In some cases, the AMPS are chemically conjugated to the surface of pre-formed microgels to further enhance antibacterial responses. All physiochemical characterization and in vitro studies are performed at n≥3, with three internal replicates per experiment. Statistical significance between conditions is evaluated using un-paired Student's t-test assuming unequal variance (p<0.05).

Experiment 2: Combinatorial Activity of Drug-Loaded Microgels

Figure 5:
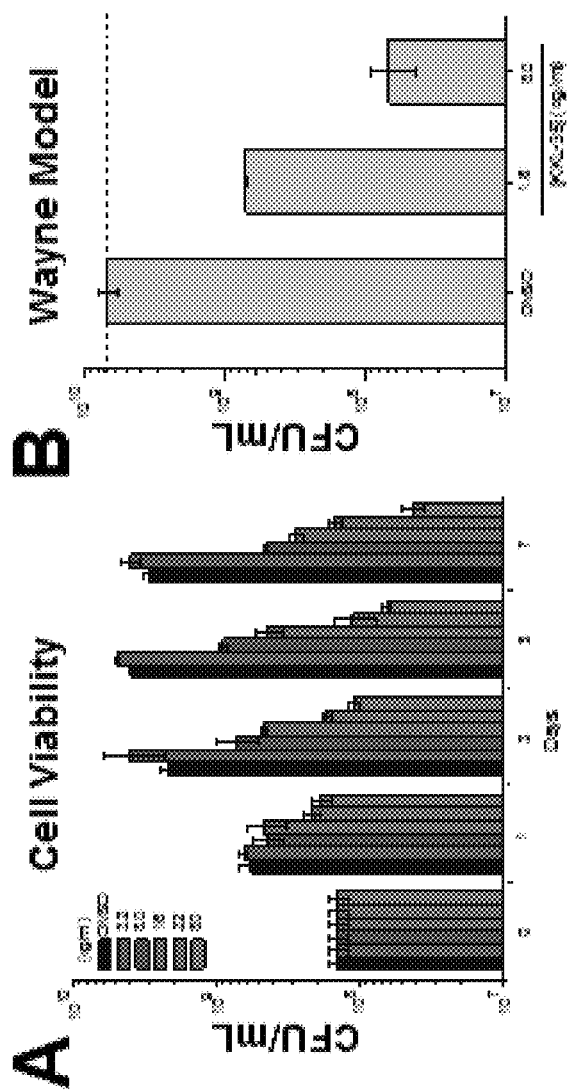
FIG. 5B is a plot of the viability of MTb under the "Wayne model." Non-replicating but viable MTb cultures were generated by gradual consumption of oxygen inside sealed glass tubes. KKL-35 was injected anaerobically and cultures stirred for 3 days. Viable bacteria were enumerated by plating. The dashed line shows CFU/mL at the time of addition.

Research has shown that the trans-translation pathway is essential for MTb growth in culture (Keiler, Nat. Rev. Micro. 2015, 13 (5), 285-297). Using bacterial reporter systems and biochemical assays, it has been demonstrated that select oxadiazole compounds inhibit trans-translation but not translation (Ramadoss, et al., Proc. Nat. Acad. Sci. U.S.A. 2013, 110 (25), 10282-10287). High-throughput screening of >660,000 compounds identified a lead agent, KKL-35, with potent activity (IC<1.6 µg/mL) towards growing MTb (FIG. 5A) and dormant persister cells (FIG. 5B), while being non-toxic towards human HeLa cells (IC>500 µg/mL, not shown).

In parallel with the formulation experiments in Aim 1, the loading and delivery of the approved TB antibiotic rifampicin (RIF), as well as the investigational trans-translation inhibitor KKL-35, from microgels is examined as individual agents or co-loaded into the same particle. Of note, although microgels may be able to deliver many different classes of antibiotics, RIF was selected for initial studies as it is a first-line TB drug that is challenged by low water solubility and dose-limiting side effects (Laurenzi, et al., Infectious Disorders-Drug Targets 2007, 7 (2), 105-119), thus making it an ideal model with which to test the drug formulation and delivery capabilities of microgels. Loading is performed by dissolving each compound in the HA electrospray solution at its maximum water soluble concentration (10 mg/mL for RIF (R3501, S. P. N., RIFAMPICIN. In Product Information Sheet, Sigma-Aldrich: 1997), 500 µg/mL for KKL-35), leading to direct encapsulation of the drug within microgels following AMP cross-linking. To evaluate the influence of HA molecular weight on enzyme-mediated drug release from microgels, drug-loaded particles are formed using commercially available HA of molecular weight 10 kDa, 100 kDa and 1 MDa. The length of HA is a particularly important parameter as high molecular weight variants not only undergo slower enzymatic degradation, but are also known to inhibit pulmonary inflammation and epithelial destruction during bacterial infection (Cyphert, et al., Int. J. Cell Biol. 2015, 2015, 8). At any rate, drug loading efficiency is established by pelleting a known mass of freshly prepared microgel particles via centrifugation (10,000 rpm for 5 min), and quantifying the concentration of non-encapsulated drug remaining in the supernatant via HPLC. The RIF loading is determined by measuring the absorbance of purified particles at the drug's characteristic UV maxima ($\lambda_{max}$=500 nm; Pati, et al., Sci. Rep. 2016, 6, 24184). Loading results are expressed as the weight of drug encapsulated per unit mass of the microparticles, with an ideal load of ≥40 µg/mg. This threshold is based on previous experiments demonstrating that a similar RIF loading into PLGA microspheres produced effective anti-TB responses in vitro and in vivo (O'Hara and Hickey, Pharm. Res. 2000, 17 (8), 955-961; Suarez, et al., Pharm. Res. 2001, 18 (9), 1315-1319).

Drug release from microgels in the absence or presence of physiologically relevant concentrations of hyaluronidase enzymes HYAL1 and 2 (50 µg/mL) (Sahu, Biochem. Med. 1981, 25 (1), 56-61) is measured as a function of HA molecular weight and incubation time (0-72 hours). At selected time points after enzyme addition, samples are centrifuged to pellet intact particles and the supernatant assayed by LC-MS. Concentration of released drug is determined from LC peak areas relative to calibrations, and results are normalized to initial loaded concentration to calculate percentage cumulative release. Tandem MS monitors potential decomposition of the antibiotics during enzyme-mediated particle degradation and release. Formulations that retain the drug when incubated in blank buffered control solutions, but allow for sustained multi-day release of the cargo in the presence of hyaluronidase, are carried forward for in vitro assays. Collectively, these studies identify the design criteria that governs drug release from AMP microgels, and allow for optimization of particle formulations to achieve long-term delivery of therapeutically relevant drug concentrations to physiologic solutions.

The therapeutic activity of drug-loaded microgels towards growing and non-replicating dormant MTb is evaluated through a series of aerobic and anaerobic cell-based assays, respectively. Single or dual drug-loaded formulations are added to aerobic MTb cultures (H37Ra) seeded into multi-well plates, and bacterial growth is evaluated as a function of particle concentration (0.001-10 mg/mL) and incubation time (1-5 days). Similar experiments in non-proliferating persister cells are performed using the anaerobic 'Wayne' model, in which non-replicating but viable MTb cultures are generated by gradual oxygen consumption in a sealed glass vial. Microgels suspended in buffer are then introduced to the cultures anaerobically via a septum, followed by stirring of the cultures for 3 days and viable bacteria quantified by plating. For both experiments, cultures left untreated, or lysed using Triton X-100, serve as negative and positive controls, respectively. Results are compared to MTb incubated with blank AMP microgels, or an equivalent concentration of the free antibiotic, to identify potential synergy between AMPS and small molecule drugs. Microgels with activity equal to, or greater than, the free antibiotic control after a single dose are subjected to screening against virulent and drug-resistant MTb through the NIAID TB research program.

These studies optimize antibiotic combination and particle composition to afford drug-loaded microgels with sufficient potency ($IC_{90}$<50 µg/mL; threshold based on limitations of material yield and lung volume). These studies demonstrate that drug-loaded AMP microgels lead to more potent and sustained anti-TB activity than the standard of care of a bolus dose of antibiotics. In cases of poor drug solubility in the aqueous HA electrospray solution and low loading efficiencies, DMSO is added (up to 5% v/v) until loading above the objective threshold (≥40 µg/mg for RIF) is achieved. For RIF in particular, a lactose blend is employed (90:10 RIF:lactose) previously shown to enhance RIF loading into PLGA microspheres (O'Hara and Hickey, Pharm. Res. 2000, 17 (8), 955-961). In some cases, changing HA molecular weight to modulate the enzymatic degradation of microgels is not sufficient on its own to effectively control the rate of drug release. In cases where release is too slow, as indicated by sub-therapeutic concentrations of drug released after 3 days, the porosity of the microgel matrix is increased by reducing the concentration of the AMP cross-linker. Otherwise, salt leeching is employed to increase the porosity of cross-linked materials (Annabi, et al., Tissue Eng. B, Rev. 2010, 16 (4), 371-383).[44] In cases where drug release is too rapid, such that complete release occurs within hours, drug diffusion is slowed by employing high AMP concentrations to increase particle matrix density, or by including polylysine as a co-crosslinker. To obtain rigorous and reproducible results, drug release and in vitro studies are performed at n≥3, with three internal replicates per experiment. Statistical significance is established via one-way ANOVA (p<0.05).

Experiment 3: Microgel Sterilization of Infected Macrophages and Cargo Delivery into Granulomas The incubation time required for microgel phagocytosis by macrophages is optimized using live-cell fluorescence microscopy. Here, differentiated THP-1 cells are incubated for 0.5-6 hours with rhodamine-labeled AMP microgels (prepared as described elsewhere herein) at a 1:25 cell: particle ratio (Pacheco, et al., PLoS One 2013, 8 (4), e60989). Treated macrophages are counterstained with calcein-AM and DAPI to visualize cells and confirm intracellular uptake of rhodamine-labeled particles. The ability of drug-loaded microgels to clear MTb from infected macrophages is tested using an in vitro co-culture infection model (Estrella, et al., Front. Microbiol. 2011, 2, 67). Briefly, differentiated THP-1 cells are incubated with MTb (H37Ra) at a multiplicity of infection of 10 for 24 hours to allow for microbe uptake. Cells are then washed to remove non-phagocytosed bacteria, seeded into multi-well plates and treated with drug-loaded microgels at 0.1-10 mg/mL concentrations to initiate particle phagocytosis. After the predetermined treatment period, cells are washed to remove un-internalized particles and incubated for an additional 5 days in blank medium. Changes in the bacterial load of treated macrophages are quantified by directly counting the number of bacilli per cell. To this end, treated cells are fixed, stained with the mycobacterium specific marker auramine-rhodamine, and counter-stained with DAPI to visualize THP-1 cells before performing fluorescent microscopy. In parallel experiments, treated macrophages are lysed, the lysate plated onto agar, and the samples incubated for 2 to 3 weeks to determine the intracellular CFU load. For both of these studies, results are compared to control samples of untreated infected macrophages, cells incubated with blank microgels, or those given free antibiotic(s), to assess the enhanced efficacy of drug-loaded microgels relative to free drug.

The delivery of antibiotics and AMPS into granuloma tissue is tested using a modified in vitro model (Sarathy, et al., JoVE 2017, (123), e55559). In brief, PMA-activated THP-1 cells are incubated with 0.4 mM oleic acid overnight to form foamy macrophages. These cells are then pelleted, lysed and denatured at 75° C. to produce a cell amalgam, 'caseum', that mimics the composition and architecture of necrotic TB lesions. The caseum pellets are sectioned into ~11 mm discs and placed into 24 well plates. To initiate treatment, cell culture media containing viable PMA-activated THP-1 cells and 0.1-10 mg/mL of selected drug-loaded microgels, or an equivalent concentration of free drug as a control, is added to each well and incubated for 5 days. This procedure allows for uptake of microgels into macrophages and their subsequent incorporation into the necrotic granuloma lesion. Following treatment, the caseum samples are washed, embedded in paraffin and sectioned using a hand microtome to allow for analysis via time-of-flight secondary ion mass spectrometry (ToF-SIMS). Importantly, ToF-SIMS can detect the presence of defined molecular weight species across a sample surface, and thus allows for the construction of a 3D map to visualize the spatial localization of delivered AMPS and antibiotics within the model tissue. Results are compared to control samples treated with an equivalent concentration of the free antibiotic(s).

These studies test the capacity of drug-loaded microgels to clear MTb within infected macrophages, and assesses their ability to enhance the penetrance and delivery of therapeutic cargo within granuloma tissue. These studies allow for the translation of selected microgel formulations into preclinical animal models. Uptake of microgels into THP-1 cells is not a significant problem, as the rapid phagocytosis of HA microparticles into macrophages is known (Kamat, et al., Bioconj. Chem. 2010, 21 (11), 2128-2135). In cases where poor MTb clearance is observed in the co-culture infection assay, multi-drug cocktails typically used in the clinic (e.g. RIF, isoniazid, pyrazinamide and ethambutol) are encapsulated and delivered. Ambiguous ToF-SIMS analyses of the in vitro model granuloma tissue are further confirmed using rapid equilibration dialysis (RED) experiments (Sarathy, et al., JoVE 2017, (123), e55559). THP-1 cell pellets are homogenized, mixed with drug-loaded microgels and placed within the donor chambers of RED inserts. Blank buffer is placed in the cognate receive chamber, and samples incubated for 4 hours. Subsequent LC-MS analysis of the donor and receiver chamber allow for the quantification of the amount of antibiotic retained within the caseum tissue treated with drug-loaded microgels relative to control samples incubated with the free drug. To obtain rigorous and reproducible results, in vitro studies are performed at n≥3, with three internal replicates per experiment. Statistical significance is established via unpaired Student's t-test assuming unequal variance ($p<0.05$).

Experiment 4: Biohybrid Peptide Nanogels that Augment the Utility of Bioactive Cargo Bioresponsive nano-carriers formed from readily available organic building blocks, selected from the list of generally recognized as safe (GRAS) compounds by the U.S. Food and Drug Administration, have been developed. A small library of GRAS components were systematically screened under electrospray ionization conditions to identify combinations that form physically cross-linked nanomaterials in high yield and low cost. Table 4 shows the qualitative results of this library screening process. During these studies, it was discovered that spraying hyaluronic acid (HA) nanodroplets into a bath of ϵ-poly-L-lysine (PLL) templated the assembly of the polycation into electrostatically complexed 'gel-like' nanoparticles, herein referred to as a nanogel (FIG. 8). This facile aqueous approach eliminates the need for toxic co-solvents common in the synthesis of many nanoparticle scaffolds, and yields gram-quantities of peptide nanogels in <1 hour and at low cost. Small molecules or proteins present during nanogel assembly are readily encapsulated within the particle matrix and can be controllably released upon swelling of the carrier in physiologic solutions. A series of biophysical and cell-based assays demonstrate that peptide nanogels augment and enhance the utility of delivered cargoes; notably improving the potency of loaded antibiotics and chemotherapeutics, as well successfully delivering otherwise membrane-impermeable proteins to the cytoplasm of treated cells. Peptide nanogels represent a novel class of bioresponsive carriers that can improve the therapeutic and diagnostic utility of bioactive payloads challenged by poor cell permeability, low bioavailability and limited solubility.

TABLE 4

Qualitative studies of GRAS components for nanoparticle formation

| | | Anion | |
|---|---|---|---|
| | | Hyaluronic Acid (HA) | Alginate (Alg) |
| Cation | Polyethylimine (PEI) | Film | Large particles, abnormal, agglomerate/gel |
| | Calcium ($Ca^{2+}$) | No result | Microparticles, spherical, uniform |
| | poly-L-lysine (PLL) | Nanoparticles, uniform, turbid solution | Large agglomerate/gel |

Materials and Methods

Hyaluronic Acid (MW: 100 kDa) was purchased from Lifecore Biomedical (Chaska, Minn.). 0.1% (w/v) poly-L-lysine (x=400) was purchased from Alamanda Polymers (Huntsville, Ala.). Vancomycin hydrochloride and MTT powder were purchased from Chem-Impex (Wood Dale, Ill.). Green fluorescent protein was provided by the Schneider Group (NCI/NIH; Frederick, Md.). Doxorubicin hydrochloride was purchased from Oakwood Chemical (Estill, S.C.). Formic acid, LC/MS grade acetonitrile, Cation adjusted Mueller-Hinton broth and Glutamax were purchased from Thermo Fisher Scientific (Waltham, Mass.). 300 kDa MWCO dialysis tubing was purchased from Spectrum (Rancho Dominguez, Calif.). *P. aeruginosa* and *S. aureus* were provided by the Chroneos Group (Hershey Medical Center; Hershey, Pa.). *E. coli* was provided by Pak Kin Wang's Group (Dept. of Biomedical Engineering; University Park, Pa.). *A. baumannii* and *S. enterica* provided by the Keiler Group (Dept. of Biochemistry and Molecular Biology; University Park, Pa.). NL-20 cells were provided by Matthew Taylor's group (Hershey Medical Center; Hershey, Pa.). RPMI 1640 culture medium was purchased from Lonza (Basel, Switzerland). Fetal Bovine Serum (FBS), L-glutamine (L-Gln), Trypsin, Phosphate Buffered Saline (PBS) and Dulbecco's Modified Eagle Medium (DMEM) were purchased from Corning (Corning, N.Y.). Gentamicin and Ham's F12 medium were purchased from VWR (Radnor, Pa.). HUVEC (ATCC PCS-100-010), Vascular Cell Basal Medium and the Endothelial Growth Cell Kit—VEGF were purchased from ATCC. EmbryoMax Ultrapure Water with 0.1% Gelatin, MEM Non-Essental amino acid solution 100×, D-(+)-Glucose, Recombinant human insulin, Human Plasma Transferrin Apo-, Hudrocortisone, and Epidermal growth factor were purchased from Sigma Aldrich (St. Louis, Mo.).

The PLL bath solution was made by 10-fold dilution of stock solution into autoclaved DI water. The solution was filtered at 0.2 μm (polyethylene sulfone, VWR; Radnor, Pa.) and a final volume of 30 mL was achieved. The HA spray solution concentration was determined by N:P ratio, the molar ratio of negative to positive charged units (assuming all are concurrently ionized), with PLL concentration remaining constant. The HA was dissolved in autoclaved DI water at 37° C. and the solution was filtered at 0.2 μm by polyethylene sulfone with a final volume of 3 mL. The HA solution was loaded into a 5-mL syringe and attached to a 0.5 inch 28-gauge needle (Hamilton; Reno, Nev.). A load was applied from a grounded high voltage power supply (230-30R, Spellman; Hauppauge, N.Y.). The PLL bath was set in a glass petri dish with a submerged common ground wire. HA was sprayed into the bath at 0.1 mL/min (Pump 11 Elite, Harvard Apparatus; Holliston, Mass.) to a total spray volume of 2 mL. The resulting particle solution was incubated at 37° C. for 1 hour. Then the particles were centrifuged (Centrifuge 5430 R, Eppendorf; Hamburg, Germany) at 10,000×G at 25° C. for 30 minutes and washed once with autoclaved DI water. The washed particles were slow frozen in isopropanol to −80° C. and lyophilized (FreeZone 4.5, Labconco; Kansas City, Mo.) overnight if storage or later experiments required.

After the preparation of nanogels was complete, samples were characterized by dynamic light scattering (DLS) and zeta potential (Zetasizer Nano ZS, Malvern; Malvern, United Kingdom). Scanning electron microscopy (SEM; NanoSEM 630, FEI; Hillsboro, Oreg.) was employed to confirm DLS results. Nanogels in suspension were allowed to air dry directly on specimen stubs before iridium (Ir) sputter treatment.

Following the centrifugation washing, nanogels were resuspended in Dulbecco's Modified Eagle's Medium (DMEM). DLS measurements were taken immediately after resuspension, and at predetermined timepoints, until no comprehensible signal was recorded. Particle suspensions were incubated at 37° C. for the duration of the experiment, and mixed by inversion before each measurement.

Vancomycin hydrochloride was dissolved at 75 mg/mL in an HA solution prepared at an N:P of 10. The 0.01% PLL bath was made and the Vanco-HA solution was electrosprayed into the bath following the method laid out in the previous section. After centrifugation, the loaded particles (Vanco-BNCs) were resuspended in DI water. Loading was characterized by sonicating Vanco-BNCs and measuring absorbance at 280 nm on reverse-phase HPLC using a C18 analytical column from Phenomenex (Torrance, Calif.). HPLC solvents consisted of solvent A (0.1% formic acid in water) and solvent B (0.1% formic acid in 9:1 acetonitrile/water) with a linear gradient of 0-100% solvent B over 25 min.

Green Fluorescent Protein (GFP) was dissolved at 0.1 mg/mL in the 0.01% PLL bath solution. The HA solution was prepared at an N:P of 10, electrosprayed following the method described elsewhere herein. The loaded particles (GFP-BNCs) were washed following the same centrifugation method used for unloaded particles. The resulting pellet was resuspended in DI water, and filtered at 0.2 μm by centrifuge filter. Loading was characterized by measuring fluorescence ($\lambda_{ex}$=470 nm, $\lambda_{em}$=515 nm) of 100 μL in a 96 well plate on a microplate reader (Cytation 3, BioTek; Winooski, Vt.).

Unloaded BNCs were resuspended in DI water to a concentration of 2 mg/mL. Doxorubicin hydrochloride was weighed out to achieve a 1:1 particle:Dox mass ratio, solubilized in an equal volume of DI water and stirred overnight. The loaded particles (Dox-BNCs) were washed following the same centrifugation method used for unloaded particles. The resulting pellet was resuspended in DI water, and filtered at 0.2 μm by centrifuge filter. Loading was characterized by measuring fluorescence ($\lambda_{ex}$=480 nm, $\lambda_{em}$=570 nm) of 100 μL in a 96 well plate on a microplate reader.

Loaded BNCs in DI water were injected into 300 kDa MWCO dialysis tubing. The tubing was submerged in a 30× (by volume) bath of PBS. At predetermined time points, multiple samples (n≥3) were collected from multiple locations throughout the bath. These samples were pooled and release was characterized in the same method used for assessing initial loading. Before each measurement, volume was adjusted to that of the initial bath to ensure concentration consistency.

2× Dilutions of treatments in broth were plated into a U-bottom 96 well plate. Overnight cultures of *Pseudomonas aeruginosa, Escherichia coli, Acinetobacter baumannii, Salmonella enterica* and *Staphylococcus aureus* were incubated in cation adjusted Mueller-Hinton broth as advised by CLSI. Bacteria were diluted to an $OD_{600}$ of 0.002 and plated in a 1:1 volume ratio with the treatments. These cultures were incubated overnight and MIC values were assessed by visual evaluation of growth inhibition when compared to untreated samples.

Cell suspensions of A549, NCI/ADR-RES, HUVEC and NL-20 cells were plated into a 96-well plate (2×10³ cells/well) and incubated for one day in complete culture medium. A549 and NCI/ADR-RES cells were cultured in RPMI-1640 supplemented with 10% FBS, 1% L-Gln, and 0.1% gentamicin at 37° C. and 5% $CO_2$. HUVEC were cultured in Vascular Cell Basal Medium supplemented as described on ATCC in flasks coated with gelatin (0.1% for 15 minutes at 37° C.) under the same conditions. NL-20 cells were cultured in Ham's F12 as described on ATCC under the same conditions. The cells were treated after removing the previous complete medium supernatant and incubated for 48 hours before removing the treatment supernatant. Cell viability was assessed by adding 0.5 mg/mL MTT solution in complete culture medium into each well. After standard incubation for 2 hours, the cells were read with a microplate reader at 540 nm. The resulting data was analyzed using nonlinear regression of semi log data as performed by GraphPad Prism.

Cell suspensions of A549 cells were plated into a 24-well plate ($5 \times 10^4$ cells/well) with a sterile cover slip and incubated for one day in complete culture medium at 37° C. and 5% $CO_2$. The cells were treated after removing the previous complete medium supernatant and incubated for 72 hours before removing the treatment supernatant. Cells were rinsed with fresh media to remove excess treatment and fixed in 4% paraformaldehyde for 15 minutes. Hoechst stain was applied at 2 µg/mL for 15 minutes and washed with PBS. Fixed stained cultures were stored at 4° C. until imaging by confocal microscopy (FV1000, Olympus; Shinjuku, Japan).

The Results of the Experiments Will Now be Described

Figure 9:
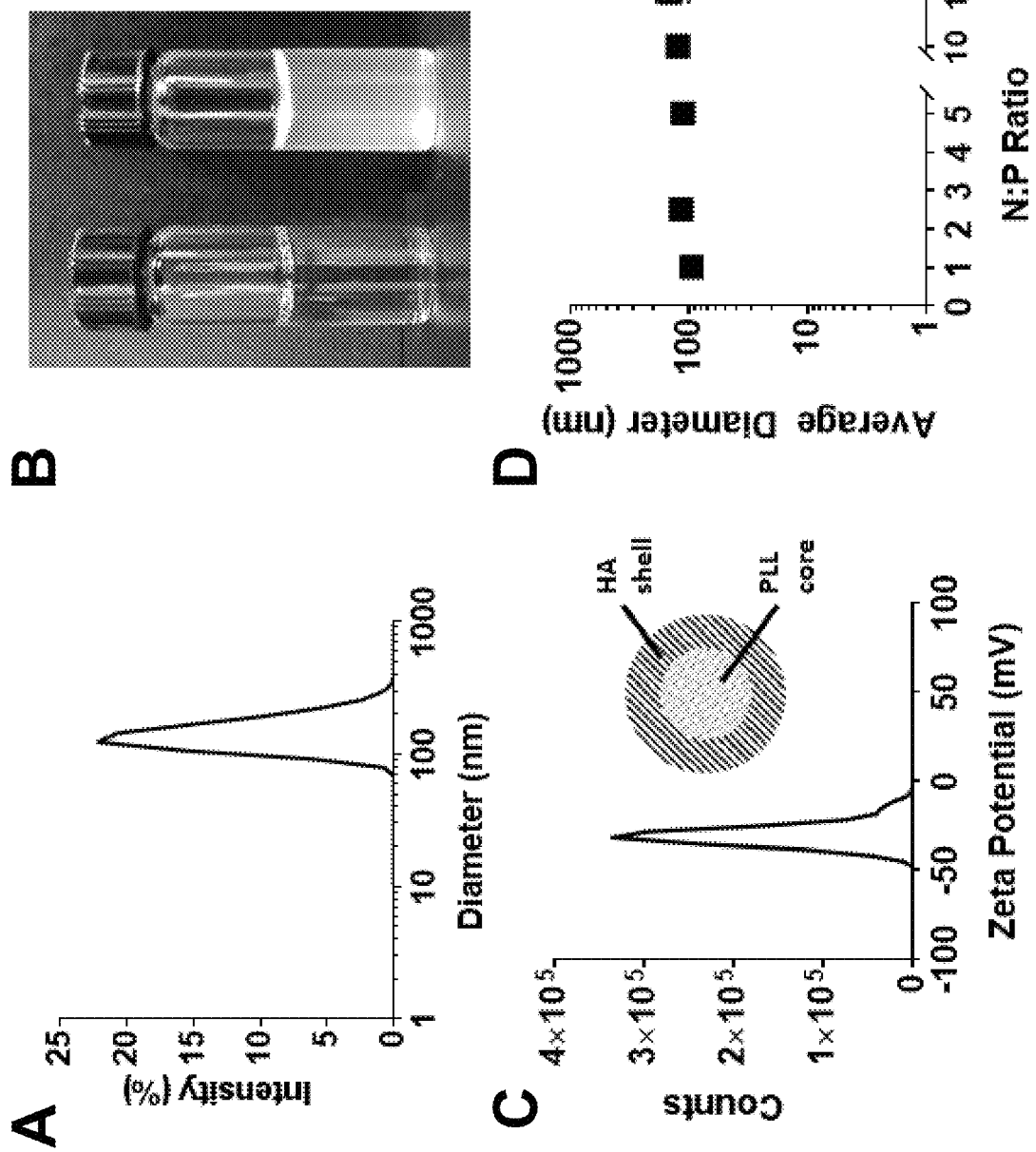
FIG. 9, comprising
Figure 10:
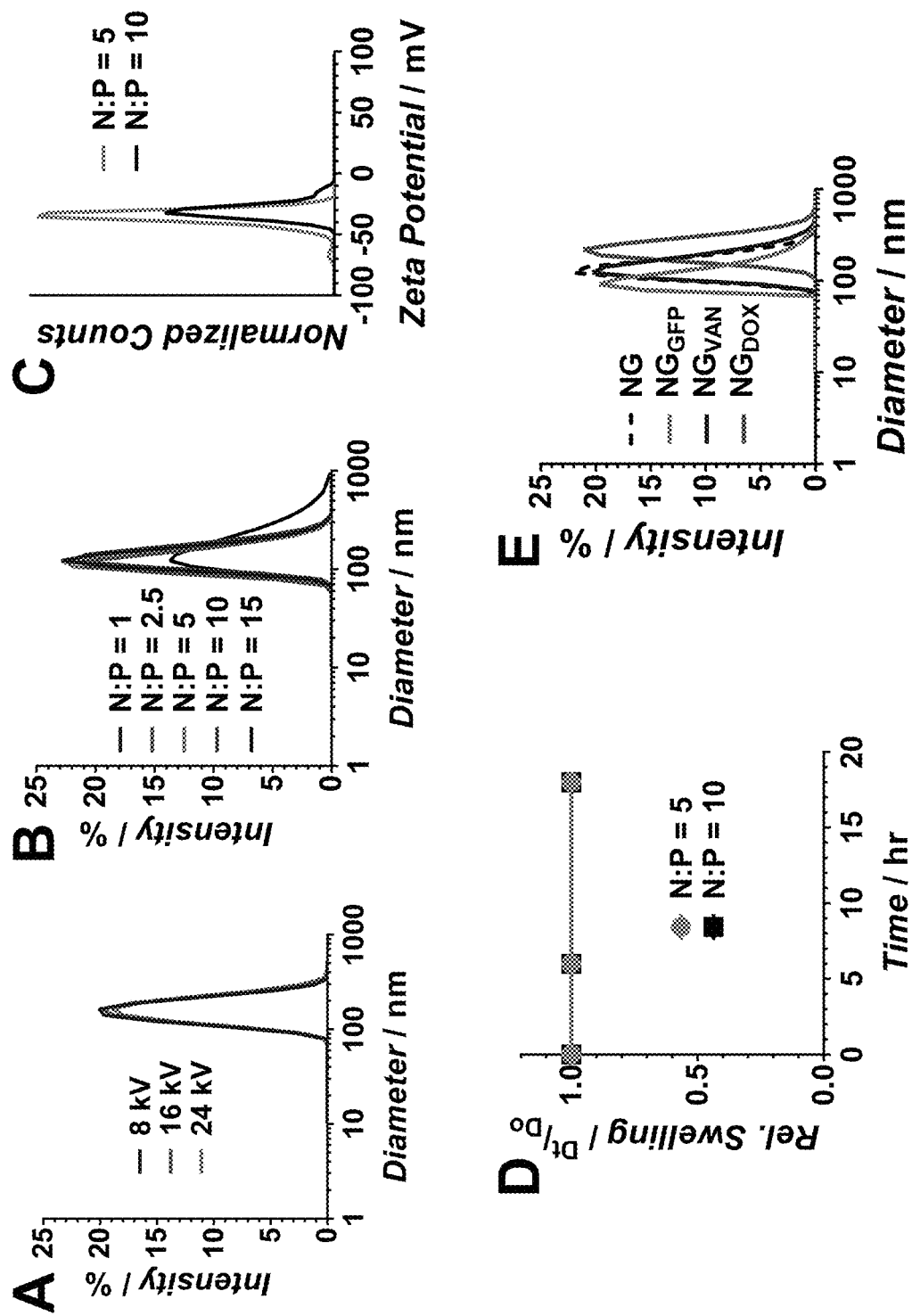
FIG. 10, comprising

Exploiting the assembly of bio-sourced and biodegradable GRAS compounds is an attractive strategy in the design of environmentally-sensitive, or 'green', engineered nanomaterials. These components are often inexpensive, readily available in bulk, and present a lower barrier to regulatory approval compared to synthetic analogues. With this in mind, a library of commercially available GRAS compounds was tested to identify suitable combinations under which bioresponsive nanoparticles could be prepared via electrospray ionization. Electrospraying is a procedure by which a high voltage is applied to a sample solution as it's passed through a capillary tip. Coulombic repulsion within the ejected solution generates a fine nanodroplet mist that is collected in a bath solution containing the complimentary cross-linker. This facile synthesis method provides a convenient means to rapidly screen different permutations of oppositely charged molecules to assess their potential to form competent nanomaterials in bulk. During these studies it was observed that many of the electrosprayed GRAS mixtures generated surface films, fibrous amalgams or large amorphous aggregates. However, one particular combination of spraying a solution of hyaluronic acid (HA) into a bath of poly-L-lysine (PLL) rapidly generated a monodisperse suspension of ~120 nm particles (FIG. 9A), which remained colloidally stable in bulk solution (FIG. 9B). Interestingly, the final size of assembled peptide nanogels appeared to be insensitive to changes in the voltage applied to the metal capillary tip during electrospray synthesis (FIG. 10A).

To better understand the relative distribution of the HA and PLL components within the nanogel matrix zeta potential measurements were employed to probe the particle's surface composition. FIG. 9C shows that nanogels possess a highly electronegative surface (−35 mV), indicating that the particles are likely comprised of an anionic HA shell that surrounds a PLL-rich core. Next, we tested how the density of electrostatic cross-links in the particle network impacts the size of assembled nanogels. This was done by adjusting the concentration of HA in the spray to vary the stoichiometric ratio of negative (N; $COO^-$ of HA) to positive (P; $NH_3^+$ of PLL) groups available to assemble the final particle matrix. We found that varying the N:P ratio from 1 to 15 formed peptide nanogels of uniform size (FIG. 9D, FIG. 10B). Further, we observed a similar surface charge for particles prepared at an N:P of 5 and 10, suggesting that the core-shell architecture of nanogels is not influenced by the relative number of cross-links that comprise the matrix (FIG. 10C). Attempts to form nanogels at N:P ratios <1 resulted in instable particles that could not be accurately measured by DLS or zeta potential analysis. Collectively, these results indicate that the cross-linking density of the nanogel network can be carefully tuned, independent of the final particle size, and in turn may allow for control over the swelling behavior of the particles in physiologic solutions.

Figure 11:
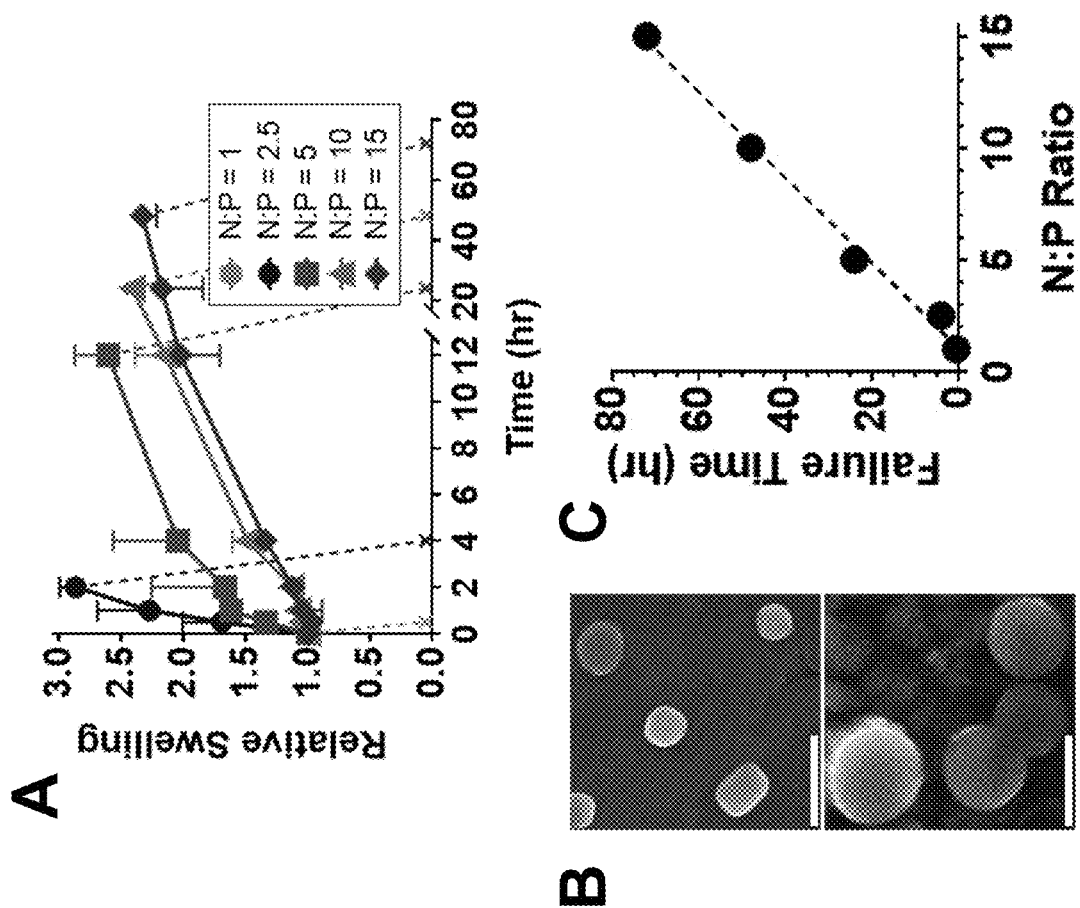
FIG. 11, comprising

In order to test the above assertion, nanogels formulated with different N:P ratios were suspended in 37° C. cell culture media and measured the change in particle size as a function of time. FIG. 11A shows that the rate of nanogel swelling is inversely related to the amount of HA in the network. Further, the time to particle failure, or the point at which the network can no longer sustain a competent gel, increased from 1-72 hours as the N:P ratio was raised 1 to 15. Interestingly, nearly all of the tested nanogel compositions reached a maximum swollen diameter of ~300 nm, representing an approximate 2.5-3.0 fold increase in size, before complete decomposition (as indicated by disappearance of the DLS signal). Conversely, nanogels suspended in deionized water remained stable and showed no time-dependent change in size (FIG. 10D). Scanning electron microscopy (SEM) performed on particles before and after swelling demonstrates that peptide nanogels possess a smooth surface topology that is maintained during their expansion, without apparent fragmentation or particle agglomeration (FIG. 11B). Together, these results suggest that disruption of the nanogel electrostatic matrix by infiltrating salt ions leads to bulk expansion of the biopolymer network. The matrix continues to swell until a critical entanglement threshold is reached and particle integrity is lost. Importantly, the time to nanogel failure is linearly dependent with the N:P ratio used during their synthesis (FIG. 11C). This suggests that nanogel decomposition can be carefully controlled with high temporal resolution to afford precise release of encapsulated cargo.

Figure 12:
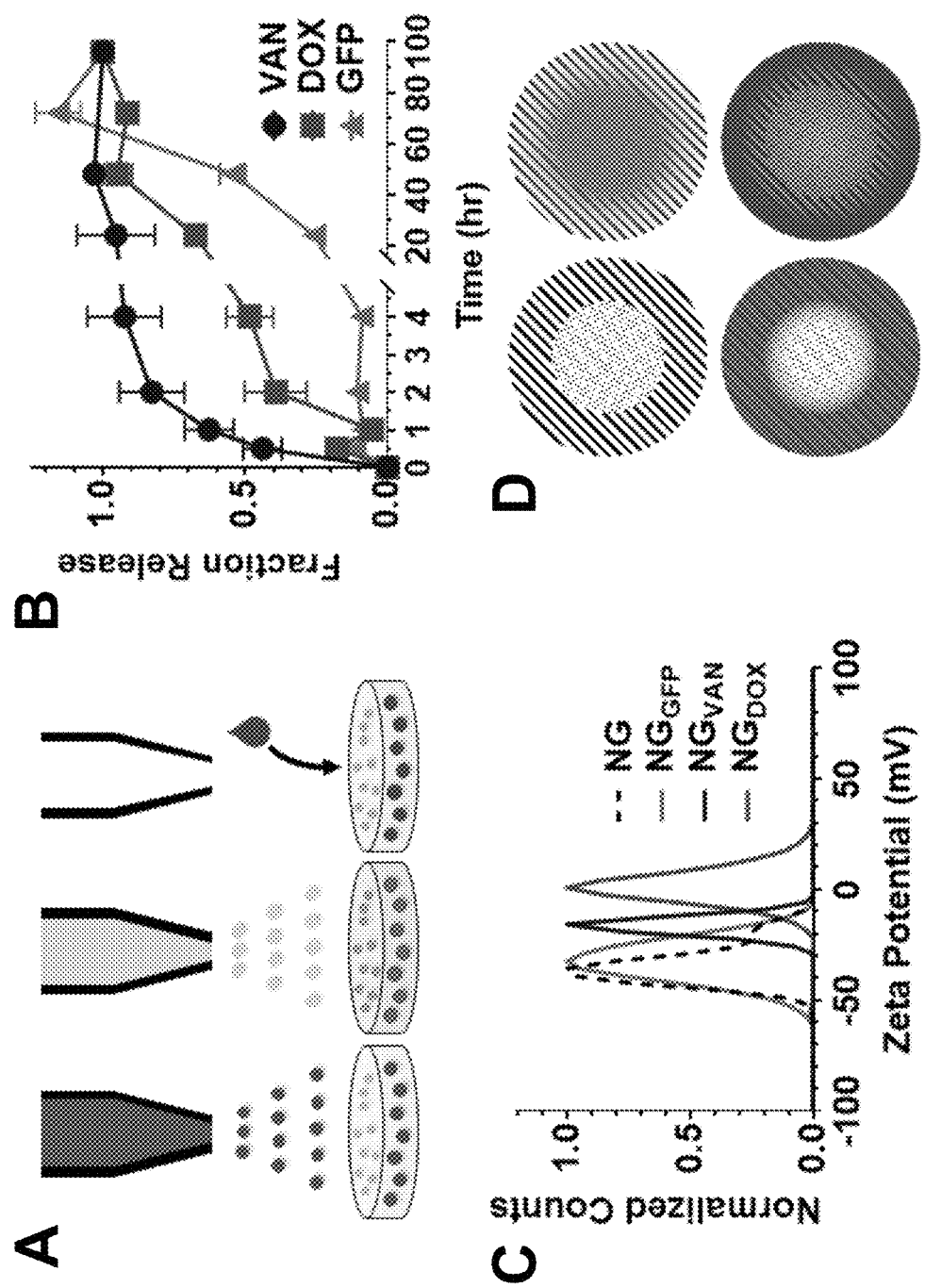
FIG. 12, comprising
Figure 13:
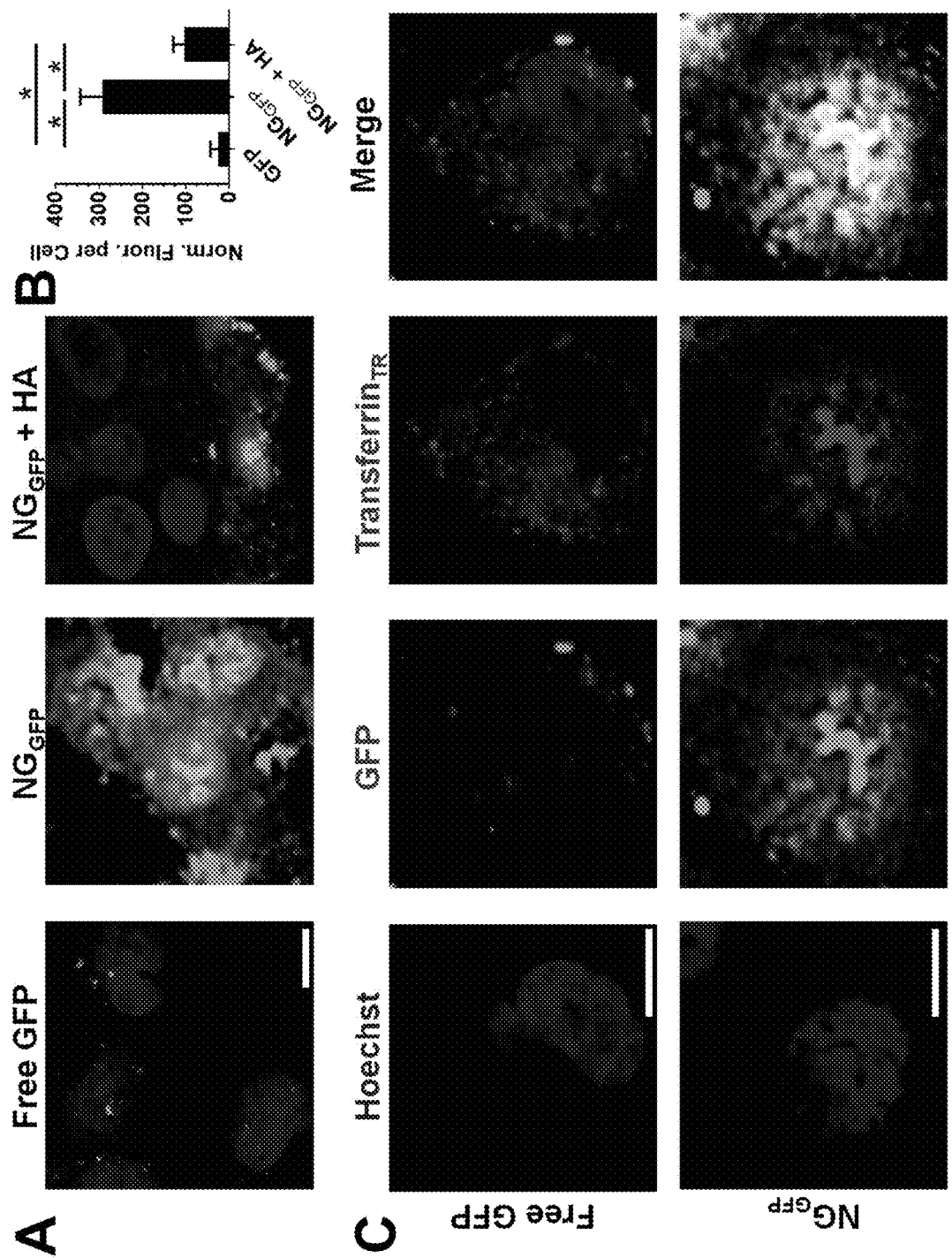
FIG. 13, comprising

To demonstrate the utility of nanogels for drug delivery applications, a series of release experiments were perfomed following the encapsulation of three different molecular cargoes: the model biomacromolecule green fluorescent protein (GFP), the small molecule chemotherapeutic Doxorubicin (Dox), and the antibiotic Vancomycin (VAN). Nanogels formed from an N:P of 10 were used in these studies, as these particles could be readily prepared in bulk and showed a multi-day swelling profile amenable to sustained drug delivery (FIG. 11A). Loading of the various cargoes into the nanogel carrier was performed using three different optimized procedures (FIG. 12A). This included incorporation of the agent in the sprayed HA solution (VAN) or the PLL bath (GFP), leading to its direct encapsulation during particle assembly. In the case of DOX, incubating pre-assembled nanogels with the hydrophobic drug led to optimal loading. Attempts to include DOX in the spray or bath solutions led to amorphous precipitates during particle assembly. At any rate, these varied loading methods highlight the ability of the nanogel electrospray synthesis procedure to be readily adapted for effective encapsulation of a variety of cargoes with vastly different solubility and physiochemical properties. DLS analysis confirmed that loading of the different agents into the nanogel carrier did not significantly impact their size (FIG. 10E).

Next, physiologic release of the encapsulated cargo was assessed by loading each nanogel formulation into a dialysis cassette and suspending it in a release media of 37° C. PBS.

The concentration of loaded drug or GFP liberated to the dialysis media was then monitored as a function of time via UV-Vis or fluorescence spectroscopy, respectively. Results in FIG. 12B show that the hydrophilic drug VAN is rapidly released from the nanogel carrier with first order kinetics, achieving 90% drug release within 4 hours. DOX, on the other hand, displays a zero-order release rate of ~4%/hour, leading to its complete release after 48 hours. Interestingly, GFP loaded formulations showed a very different release profile. The majority of encapsulated protein (>75%) was retained within the nanogel carrier for the first 24 hours, followed by a rapid release phase that occurred between 24 and 72 hours. Taken together with the nanogel swelling data (FIG. 11A), this suggests that much of the loaded macromolecular protein remains entrapped within the carrier network as it swells, and only achieves complete release upon particle disruption.

Varying the cross-linking density of the nanogel carrier, as well as the physiochemical properties of the cargo, can be used to carefully control the release profile of loaded agents. To better understand how the method of encapsulation impacts distribution of the cargo within the carrier, and thus influences its release, zeta potential analysis was performed on the loaded formulations (FIG. 12C). Unloaded control nanogels (NG) are characterized by a surface zeta potential of ~35.3 mV, which did not significantly change when GFP is encapsulated within the carrier ($NG_{GFP}$). This suggests that the protein is largely sequestered within the PLL-rich core (see schematic representation in FIG. 12D). Here, suspension of the negatively charged GFP protein, which possess an isoelectric point of ~5.8, in the electrospray bath solution likely leads to its initial complexation with the cationic PLL cross-linker before nanogel assembly. Conversely, as VAN is contained in the HA spray solution, the drug is entrapped within the HA nanogel corona and thereby partially passivates its electronegative surface charge. This is corroborated by zeta potential measurements, which show an increase in the surface charge of VAN-loaded nanogels to ~15.4 mV. Finally, DOX loaded formulations showed a complete neutralization of particle surface charge as indicated by a zeta potential of 0.6 mV. This is a result of the loading method employed for DOX encapsulation, in which pre-formed nanogels were incubated with a saturated solution of the drug to drive it into the particle network. At these saturating concentrations, it's likely that a fraction of the unloaded DOX molecules coat the particle surface and thus neutralizes its exterior charge. It is worth noting that due to the small size of peptide nanogels (~120 nm) more advanced analytical methods, such as confocal microscopy or TOF-SIMS, could not be applied to better assess the distribution of loaded molecules within the particle network. The data suggest that, in addition to nanogel N:P ratio and physiochemical properties of the loaded agents, the method of encapsulation can be varied to control sub-particle localization of the cargo and hence provide an additional degree of freedom to tune release.

Based on the favorable protein and drug release profiles from peptide nanogels, the delivery potential of the particles was assessed using three independent in vitro experiments. The first involved incubating GFP-loaded nanogels with cancer cells to evaluate intracellular delivery of the protein cargo using fluorescent confocal microscopy (FIG. 13). These studies revealed a remarkable capacity of nanogels to shuttle membrane-impermeable GFP proteins into cells (FIG. 13A), leading to a >11 fold enhancement in intracellular fluorescence compared to cells treated with the free protein (FIG. 13B). To investigate potential mechanisms behind the preferential uptake of $NG_{GFP}$, competitive inhibition experiments were performed in which cells were co-incubated with GFP-loaded particles and an excess of free HA (750 ug/mL). These studies evaluate the contribution of HA carbohydrates contained within the nanogel matrix, which bind to CD44 cell-adhesion receptors expressed on the surface of mammalian cells, towards endocytic uptake of the particles. Images in FIG. 13A show that an excess of free HA present in solution leads to a substantial decrease in $NG_{GFP}$ uptake, resulting in an approximate 3 fold loss of intracellular fluorescence compared to cells treated with the particle alone (FIG. 13B). Next, we co-stained free GFP or $NG_{GFP}$ treated cells with fluorescently-labeled transferrin, a marker for receptor-mediated endocytosis. The merged fluorescent images shown in FIG. 13C indicate that $NG_{GFP}$ treated cells are characterized by an approximately equal fraction of intracellular GFP delivered to the cytoplasm (green only) or co-localized with endosomes (yellow). Collectively, this data suggests that $NG_{GFP}$ particles are internalized into cells via CD44 receptor-mediated endocytosis, where a portion of the particles then subsequently escape to accumulate in the cytoplasm. This suggests that biomacromolecules delivered by peptide nanogels into cells can be transported to the cytoplasm to avoid long-term sequestration within endosomes and lysosomes.

Non-drug-loaded microgels prepared using antimicrobial peptides as the cationic polymer display remarkable activity against gram-negative bacteria relative to mammalian lung epithelial cell controls (FIG. 14A). In a second set of experiments, the chemotherapeutic potency of DOX delivered from the nanogel carrier towards drug-sensitive (A549) or DOX-resistant (NCI/ADR-RES) cells was evaluated (FIG. 14B). Free DOX demonstrates an $IC_{50}$ of 0.4 μg/mL (0.7 μM) and 6.5 μg/mL (12.0 μM) towards A549 and NCI/ADR-RES, respectively. Gratifyingly, delivery of DOX via the nanogel carrier resulted in a marked increase in drug potency towards both cell lines. For example, treatment of A549 cells with $NG_{DOX}$ resulted in a >10-fold enhancement in drug cytotoxicity ($IC_{50}$=0.03 μg/mL; 0.06 μM of equivalent drug), compared to samples treated with free DOX. Control samples treated with empty nanogels (NG) show the un-loaded carrier is well tolerated by both cell lines.

Next, the antibacterial activity of VAN-loaded nanogels were evaluated against a panel of gram-negative and gram-positive bacterial pathogens (Table 5). It is important to note that clinical use of VAN is generally excluded to gram-positive infections as most gram-negative pathogens are innately resistant to the drug. This is due to the thick outer membrane of gram-negative bacteria which prevents the large glycopeptide drug from diffusing into the cell wall and reaching its enzymatic target. Not surprisingly then, weak activity of VAN was observed towards four different gram-negative pathogens, leading to inhibition of bacterial growth only at the highest concentration tested (144 μg/mL). Conversely, the drug was >30 times more effective in killing the control gram-positive strain *Staphylococcus aureus* (*S. aureus*).

TABLE 5

Minimum inhibitory concentration (MIC) of free VAN, VAN-loaded nanogels ($NG_{VAN}$) or the empty nanogel carrier (NG) against a panel of gram-negative (−) bacteria, or the model gram-positive pathogen S. aureus (+). Results are shown as the MIC of the drug, or the equivalent concentration of drug loaded into nanogels, as well as the corresponding amount of the carrier (represented as VAN | NG carrier).

| | MIC of VAN NG Carrier [µg/mL] | | | | | | | | |
|---|---|---|---|---|---|---|---|---|---|
| | P. aeruginosa (−) | | A. baumannii (−) | | S. enterica (−) | | E. coli (−) | | S. aureus (+) | |
| VAN | 144* | NA | 144* | NA | 144* | NA | 144* | NA | 4.5 | NA |
| $NG_{VAN}$ | 72 | 44 | 72 | 44 | 72 | 44 | 36 | 22 | 0.3 | 0.2 |
| NG | NA | >100* | NA | >100* | NA | >100* | NA | >100* | NA | >0.3* |

NA = not applicable.
*indicates maximum concentration tested.

Remarkably, when VAN is loaded into the nanogel carrier, significant increases in its potency towards both gram-negative and gram-positive bacteria were observed. For example, treatment of E. coli with VAN-loaded nanogels led to an equivalent drug MIC of 36 µg/mL, a 4-fold enhancement compared to the activity of free VAN. Similarly, $NG_{VAN}$ killed the gram-positive S. aureus strain at a 15-times greater potency of equivalent drug relative to bacteria treated with VAN alone. Similar to previous experiments, no toxic effects of the un-loaded nanogel carrier (NG) towards all the tested strains were observed.

Figure 14:
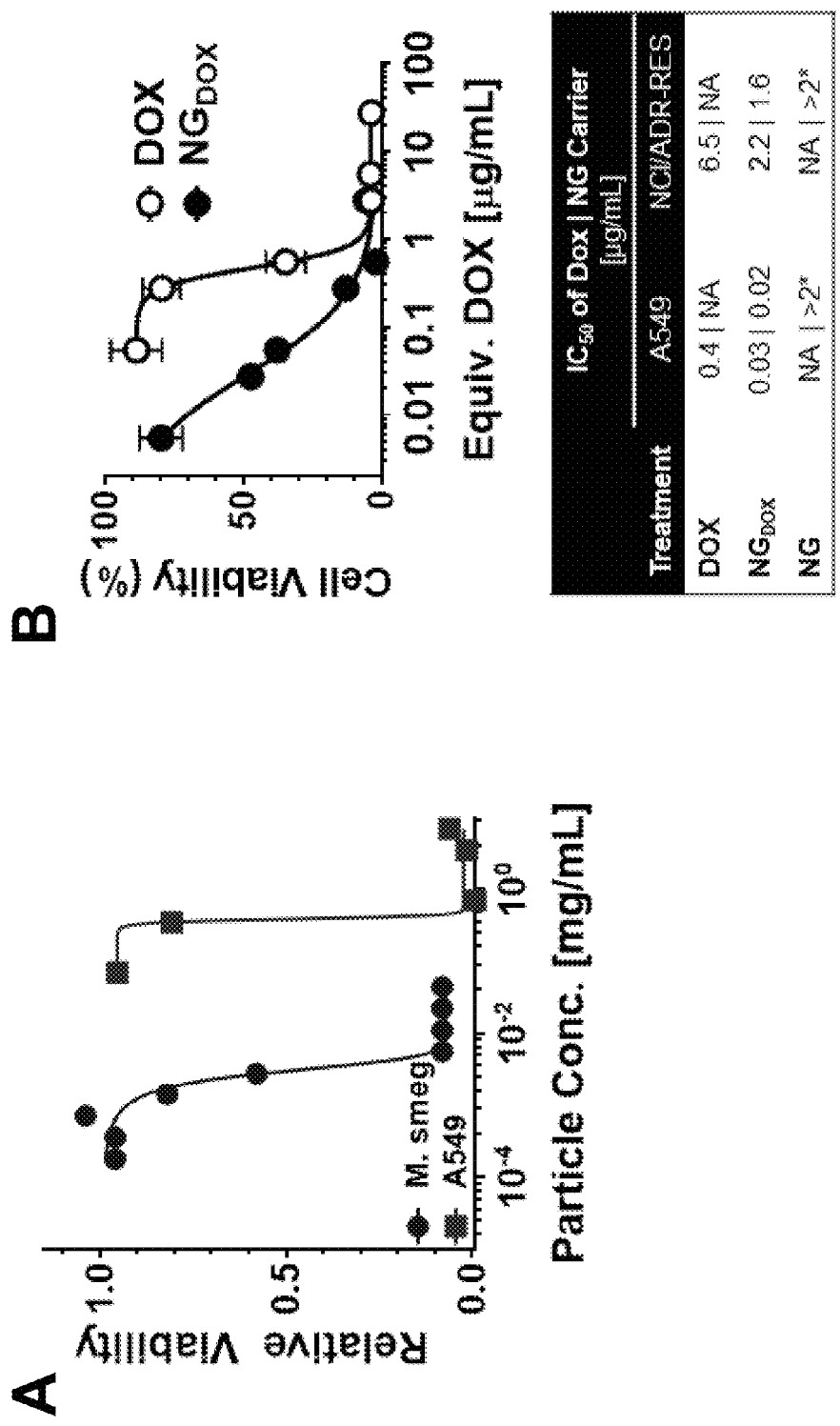
FIG. 14, comprising
Figure 15:
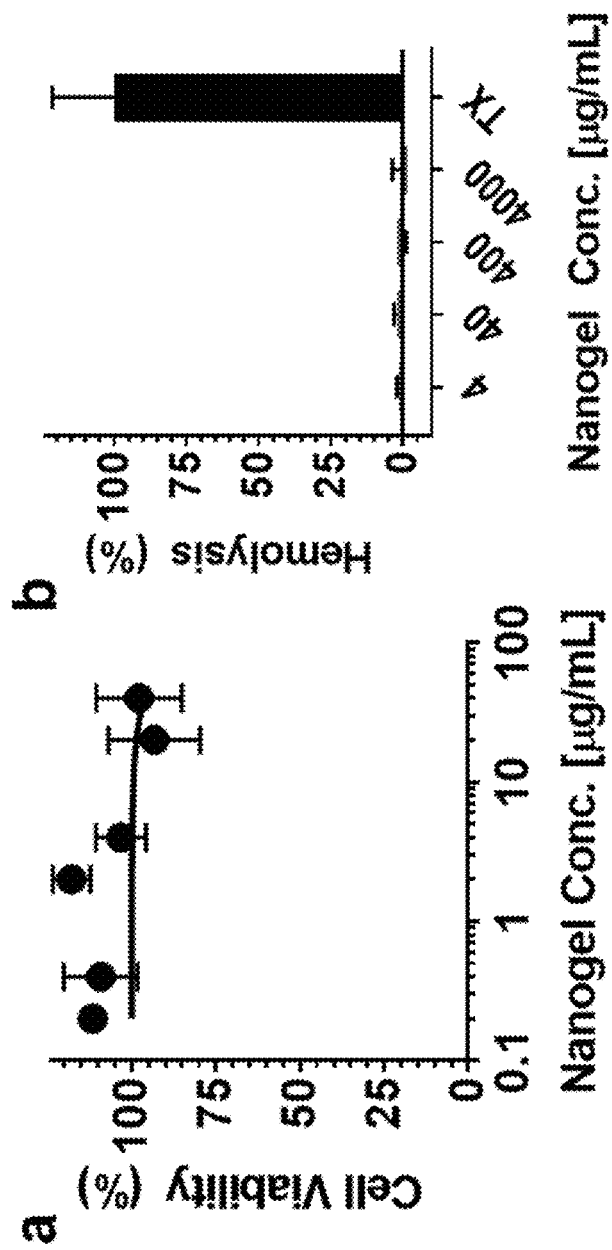
FIG. 15 shows the biocompatibility of exemplary drug delivery particles.

The biocompatibility of peptide nanogels was assessed in healthy human endothelial cells and bovine red blood cells (RBCs) following a 24 hour incubation with the particles (FIG. 15). Peptide nanogels showed no overt toxicity towards human umbilical vein endothelial cells (HUVEC), as indicated by maintenance of cell viability across a range of nanogel concentrations up to 40 µg/mL (FIG. 15A). Similarly, particles were non-hemolytic towards bovine RBCs (FIG. 15B, note 0-2% total hemolysis for all nanogel conditions) even when employed at concentrations orders of magnitude greater than what was required to achieve a therapeutic response in the DOX (FIG. 14) and VAN (Table 5) delivery studies. Collectively, these results demonstrate that peptide nanogels are a highly biocompatible delivery platform and suggest that parenteral administration of the particles to vasculature will be well tolerated.

Enhancing the utility of new therapeutic and diagnostic agents via nanoparticle-based delivery platforms requires materials that are chemically tractable, synthetically facile and are innately biocompatible. The present invention relates to a new class of peptide nanogel particle that can be rapidly prepared in high yield and purity via electrostatic complexation of complimentary charged HA and PLL biopolymers. Peptide nanogels represent a unique class of bioresponsive nanoparticles with tunable swelling and release profiles. Remarkably, nanogels display broad efficacy in a range of delivery applications, including successful delivery of a membrane-impermeable protein into cells, improving the potency of loaded chemotherapeutics towards drug-sensitive and -resistant cancer cells, and sensitization of intractable bacterial pathogens to antibiotic.

In vitro studies suggest that peptide nanogels augment the activity of delivered cargo through three potential mechanisms. First, binding of HA in the carrier matrix to CD44 adhesion receptors on the cell surface may yield a high local concentration of delivered cargo at the membrane. Second, intracellular uptake of peptide nanogels may permit more effective delivery of otherwise membrane-impermeable, or poorly permeable, into cells. Third, the cationic amphiphile PLL is known to organize with phospholipid head groups to display membrane permeabilizing effects via carpet-like mechanisms. Permeabilization of both plasma and endosomal membranes may be one mechanisms by which GFP is effectively delivered into cells via our nanogel carrier. Likewise, permeabilization of cancer or bacterial cell membranes by PLL incorporated within the particles may contribute to the marked enhancement in chemotherapeutic- and antibiotic-loaded formulations. Importantly, while these nano-scale materials are capable of augmenting the activity of loaded biosensors and drugs, they are inherently biocompatible, non-toxic and non-hemolytic. Thus peptide nanogels represent a potential theranostic platform with broad applications in drug delivery and biomedical imaging.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A plurality of drug delivery particles, comprising:
   an anionic polymer matrix; and
   a cationic polymer that is a polypeptide that has the sequence of KRWHWWRRHWVVW (SEQ ID NO:11);
   wherein the anionic polymer matrix and cationic polymer together form drug delivery particles bound by electrostatic interactions; and
   wherein the drug delivery particles comprise at least one biologically active agent.

2. The plurality of drug delivery particles of claim 1, wherein the anionic polymer matrix comprises an anionic polymer selected from the group consisting of alginic acid, arabic acid, polygalacturonic acid, poly(glucuronic acid), hyaluronic acid, heparin, N-acetyl heparin, carboxymethylcellulose, chondroitin sulfate, chondroitin sulfate B, chitin, O- or N-sulfochitosan, CM-dextran, dextran sulfate, and pectin.

3. The particles of claim, 1 wherein the plurality of drug delivery particles further comprises a cationic polypeptide that has the sequence WKWLKKWIK (SEQ ID NO:46).

4. The particles of claim 1, wherein the zeta potential of the particles is negative.

5. The particles of claim 1, wherein the at least one biologically active agent is selected from the group consisting of an antimycobacterial agent, an antimicrobial agent, an antiviral agent, an anticancer agent, and a biologic.

6. The particles of claim 1, wherein the at least one biologically active agent is selected from the group consisting of moxifloxacin, rifampicin, isoniazid, ethambutol, pyrazinamide, streptomycin, 4-chloro-N-(5-(4-fluorophenyl)-1,3,4-oxadiazol-2-yl)benzamide, vancomycin, and doxorubicin.

7. The particles of claim 1, wherein the drug delivery particles further comprise at least one pharmaceutically acceptable carrier.

8. A dry powder formulation comprising the particles of claim 1.

9. A plurality of drug delivery particles, comprising:
   an anionic polymer matrix comprising hyaluronic acid; and
   a cationic polymer comprising a polypeptide that has the sequence of KRWHWWRRHWVVW (SEQ ID NO:11);
   wherein the anionic polymer matrix and cationic polymer together form drug delivery particles bound by electrostatic interactions; and
   wherein the drug delivery particles comprise at least one biologically active agent.

10. The plurality of drug delivery particles of claim 9, wherein the at least one biologically active agent is moxifloxacin or rifampicin.

* * * * *

SEQUENCE LISTING

<160> NUMBER OF SEQ ID NOS: 55

<210> SEQ ID NO 1
<211> LENGTH: 9
<212> TYPE: PRT

```
<213> ORGANISM: Artificial Sequence
<220> FEATURE:
<223> OTHER INFORMATION: Chemically synthesized

<400> SEQUENCE: 1

Phe Phe Ile Tyr Val Trp Arg Arg Arg
1               5

<210> SEQ ID NO 2
<211> LENGTH: 13
<212> TYPE: PRT
<213> ORGANISM: Artificial Sequence
<220> FEATURE:
<223> OTHER INFORMATION: Chemically synthesized

<400> SEQUENCE: 2

Phe Ile Lys Trp Lys Phe Arg Trp Trp Lys Trp Arg Lys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Chemically synthesized

<400> SEQUENCE: 3

His Gln Phe Arg Phe Arg Phe Arg Val Arg Arg Lys
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Chemically synthesized

<400> SEQUENCE: 4

Ile Leu Pro Trp Lys Trp Arg Trp Trp Lys Trp Arg Arg
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Chemically synthesized

<400> SEQUENCE: 5

Ile Leu Arg Trp Lys Trp Arg Trp Trp Arg Trp Arg Arg
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Chemically synthesized

<400> SEQUENCE: 6

Ile Arg Met Arg Ile Arg Val Leu Leu
1               5

<210> SEQ ID NO 7
<211> LENGTH: 9
<212> TYPE: PRT
<213> ORGANISM: Artificial Sequence
```

```
<220> FEATURE:
<223> OTHER INFORMATION: Chemically synthesized

<400> SEQUENCE: 7

Lys Phe Lys Trp Trp Arg Met Leu Ile
1               5

<210> SEQ ID NO 8
<211> LENGTH: 9
<212> TYPE: PRT
<213> ORGANISM: Artificial Sequence
<220> FEATURE:
<223> OTHER INFORMATION: Chemically synthesized

<400> SEQUENCE: 8

Lys Ile Trp Trp Trp Trp Arg Lys Arg
1               5

<210> SEQ ID NO 9
<211> LENGTH: 9
<212> TYPE: PRT
<213> ORGANISM: Artificial Sequence
<220> FEATURE:
<223> OTHER INFORMATION: Chemically synthesized

<400> SEQUENCE: 9

Lys Arg Lys Lys Arg Phe Lys Trp Trp
1               5

<210> SEQ ID NO 10
<211> LENGTH: 9
<212> TYPE: PRT
<213> ORGANISM: Artificial Sequence
<220> FEATURE:
<223> OTHER INFORMATION: Chemically synthesized

<400> SEQUENCE: 10

Lys Arg Arg Trp Arg Ile Trp Leu Val
1               5

<210> SEQ ID NO 11
<211> LENGTH: 13
<212> TYPE: PRT
<213> ORGANISM: Artificial Sequence
<220> FEATURE:
<223> OTHER INFORMATION: Chemically synthesized

<400> SEQUENCE: 11

Lys Arg Trp His Trp Trp Arg Arg His Trp Val Val Trp
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Chemically synthesized

<400> SEQUENCE: 12

Lys Arg Trp Trp Lys Trp Trp Arg Arg
1               5

<210> SEQ ID NO 13
<211> LENGTH: 9
<212> TYPE: PRT
<213> ORGANISM: Artificial Sequence
<220> FEATURE:
```

```
<223> OTHER INFORMATION: Chemically synthesized

<400> SEQUENCE: 13

Lys Arg Trp Trp Arg Lys Trp Trp Arg
1               5

<210> SEQ ID NO 14
<211> LENGTH: 9
<212> TYPE: PRT
<213> ORGANISM: Artificial Sequence
<220> FEATURE:
<223> OTHER INFORMATION: Chemically synthesized

<400> SEQUENCE: 14

Lys Arg Trp Trp Trp Trp Arg Phe Arg
1               5

<210> SEQ ID NO 15
<211> LENGTH: 9
<212> TYPE: PRT
<213> ORGANISM: Artificial Sequence
<220> FEATURE:
<223> OTHER INFORMATION: Chemically synthesized

<400> SEQUENCE: 15

Lys Trp Lys Trp Trp Trp Arg Lys Ile
1               5

<210> SEQ ID NO 16
<211> LENGTH: 9
<212> TYPE: PRT
<213> ORGANISM: Artificial Sequence
<220> FEATURE:
<223> OTHER INFORMATION: Chemically synthesized

<400> SEQUENCE: 16

Leu Lys Arg Arg Trp Lys Trp Trp Ile
1               5

<210> SEQ ID NO 17
<211> LENGTH: 9
<212> TYPE: PRT
<213> ORGANISM: Artificial Sequence
<220> FEATURE:
<223> OTHER INFORMATION: Chemically synthesized

<400> SEQUENCE: 17

Leu Arg Phe Ile Leu Trp Trp Lys Arg
1               5

<210> SEQ ID NO 18
<211> LENGTH: 9
<212> TYPE: PRT
<213> ORGANISM: Artificial Sequence
<220> FEATURE:
<223> OTHER INFORMATION: Chemically synthesized

<400> SEQUENCE: 18

Leu Arg Arg Trp Ile Arg Ile Arg Trp
1               5

<210> SEQ ID NO 19
<211> LENGTH: 9
<212> TYPE: PRT
<213> ORGANISM: Artificial Sequence
<220> FEATURE:
<223> OTHER INFORMATION: Chemically synthesized
```

<400> SEQUENCE: 19

Asn Trp Arg Lys Leu Tyr Arg Arg Lys
1               5

<210> SEQ ID NO 20
<211> LENGTH: 9
<212> TYPE: PRT
<213> ORGANISM: Artificial Sequence
<220> FEATURE:
<223> OTHER INFORMATION: Chemically synthesized

<400> SEQUENCE: 20

Arg Ile Lys Arg Trp Trp Trp Trp Arg
1               5

<210> SEQ ID NO 21
<211> LENGTH: 9
<212> TYPE: PRT
<213> ORGANISM: Artificial Sequence
<220> FEATURE:
<223> OTHER INFORMATION: Chemically synthesized

<400> SEQUENCE: 21

Arg Ile Arg Arg Trp Lys Phe Arg Trp
1               5

<210> SEQ ID NO 22
<211> LENGTH: 9
<212> TYPE: PRT
<213> ORGANISM: Artificial Sequence
<220> FEATURE:
<223> OTHER INFORMATION: Chemically synthesized

<400> SEQUENCE: 22

Arg Lys Phe Arg Trp Trp Val Ile Arg
1               5

<210> SEQ ID NO 23
<211> LENGTH: 9
<212> TYPE: PRT
<213> ORGANISM: Artificial Sequence
<220> FEATURE:
<223> OTHER INFORMATION: Chemically synthesized

<400> SEQUENCE: 23

Arg Lys Trp Lys Ile Lys Trp Tyr Trp
1               5

<210> SEQ ID NO 24
<211> LENGTH: 9
<212> TYPE: PRT
<213> ORGANISM: Artificial Sequence
<220> FEATURE:
<223> OTHER INFORMATION: Chemically synthesized

<400> SEQUENCE: 24

Arg Leu Lys Arg Trp Trp Lys Phe Leu
1               5

<210> SEQ ID NO 25
<211> LENGTH: 12
<212> TYPE: PRT
<213> ORGANISM: Artificial Sequence
<220> FEATURE:
<223> OTHER INFORMATION: Chemically synthesized

```
<400> SEQUENCE: 25

Arg Leu Arg Arg Ile Val Val Ile Arg Val Phe Arg
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Chemically synthesized

<400> SEQUENCE: 26

Arg Leu Trp Arg Ile Val Val Ile Arg Val Lys Arg
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Chemically synthesized

<400> SEQUENCE: 27

Arg Leu Trp Trp Lys Ile Trp Leu Lys
1               5

<210> SEQ ID NO 28
<211> LENGTH: 9
<212> TYPE: PRT
<213> ORGANISM: Artificial Sequence
<220> FEATURE:
<223> OTHER INFORMATION: Chemically synthesized

<400> SEQUENCE: 28

Arg Leu Trp Trp Trp Trp Arg Arg Lys
1               5

<210> SEQ ID NO 29
<211> LENGTH: 9
<212> TYPE: PRT
<213> ORGANISM: Artificial Sequence
<220> FEATURE:
<223> OTHER INFORMATION: Chemically synthesized

<400> SEQUENCE: 29

Arg Gln Arg Arg Val Val Ile Trp Trp
1               5

<210> SEQ ID NO 30
<211> LENGTH: 9
<212> TYPE: PRT
<213> ORGANISM: Artificial Sequence
<220> FEATURE:
<223> OTHER INFORMATION: Chemically synthesized

<400> SEQUENCE: 30

Arg Arg Arg Ile Lys Ile Arg Trp Tyr
1               5

<210> SEQ ID NO 31
<211> LENGTH: 9
<212> TYPE: PRT
<213> ORGANISM: Artificial Sequence
<220> FEATURE:
<223> OTHER INFORMATION: Chemically synthesized

<400> SEQUENCE: 31
```

Arg Arg Arg Trp Trp Lys Leu Met Met
1               5

<210> SEQ ID NO 32
<211> LENGTH: 12
<212> TYPE: PRT
<213> ORGANISM: Artificial Sequence
<220> FEATURE:
<223> OTHER INFORMATION: Chemically synthesized

<400> SEQUENCE: 32

Arg Arg Trp Lys Ile Val Val Ile Arg Trp Arg Arg
1               5                   10

<210> SEQ ID NO 33
<211> LENGTH: 9
<212> TYPE: PRT
<213> ORGANISM: Artificial Sequence
<220> FEATURE:
<223> OTHER INFORMATION: Chemically synthesized

<400> SEQUENCE: 33

Arg Arg Trp Arg Val Ile Val Lys Trp
1               5

<210> SEQ ID NO 34
<211> LENGTH: 9
<212> TYPE: PRT
<213> ORGANISM: Artificial Sequence
<220> FEATURE:
<223> OTHER INFORMATION: Chemically synthesized

<400> SEQUENCE: 34

Arg Arg Trp Trp Lys Trp Trp Trp Arg
1               5

<210> SEQ ID NO 35
<211> LENGTH: 9
<212> TYPE: PRT
<213> ORGANISM: Artificial Sequence
<220> FEATURE:
<223> OTHER INFORMATION: Chemically synthesized

<400> SEQUENCE: 35

Arg Arg Trp Trp Arg Trp Val Val Trp
1               5

<210> SEQ ID NO 36
<211> LENGTH: 9
<212> TYPE: PRT
<213> ORGANISM: Artificial Sequence
<220> FEATURE:
<223> OTHER INFORMATION: Chemically synthesized

<400> SEQUENCE: 36

Arg Arg Tyr His Trp Arg Ile Tyr Ile
1               5

<210> SEQ ID NO 37
<211> LENGTH: 9
<212> TYPE: PRT
<213> ORGANISM: Artificial Sequence
<220> FEATURE:
<223> OTHER INFORMATION: Chemically synthesized

<400> SEQUENCE: 37

Arg Thr Lys Lys Trp Ile Val Trp Ile
1               5

<210> SEQ ID NO 38
<211> LENGTH: 9
<212> TYPE: PRT
<213> ORGANISM: Artificial Sequence
<220> FEATURE:
<223> OTHER INFORMATION: Chemically synthesized

<400> SEQUENCE: 38

Arg Trp Arg Arg Lys Trp Trp Trp Trp
1               5

<210> SEQ ID NO 39
<211> LENGTH: 9
<212> TYPE: PRT
<213> ORGANISM: Artificial Sequence
<220> FEATURE:
<223> OTHER INFORMATION: Chemically synthesized

<400> SEQUENCE: 39

Arg Trp Arg Trp Trp Trp Arg Val Tyr
1               5

<210> SEQ ID NO 40
<211> LENGTH: 9
<212> TYPE: PRT
<213> ORGANISM: Artificial Sequence
<220> FEATURE:
<223> OTHER INFORMATION: Chemically synthesized

<400> SEQUENCE: 40

Arg Trp Trp Ile Arg Ile Arg Trp His
1               5

<210> SEQ ID NO 41
<211> LENGTH: 9
<212> TYPE: PRT
<213> ORGANISM: Artificial Sequence
<220> FEATURE:
<223> OTHER INFORMATION: Chemically synthesized

<400> SEQUENCE: 41

Arg Trp Trp Arg Lys Ile Trp Lys Trp
1               5

<210> SEQ ID NO 42
<211> LENGTH: 9
<212> TYPE: PRT
<213> ORGANISM: Artificial Sequence
<220> FEATURE:
<223> OTHER INFORMATION: Chemically synthesized

<400> SEQUENCE: 42

Arg Trp Trp Arg Trp Arg Lys Trp Trp
1               5

<210> SEQ ID NO 43
<211> LENGTH: 12
<212> TYPE: PRT
<213> ORGANISM: Artificial Sequence
<220> FEATURE:
<223> OTHER INFORMATION: Chemically synthesized

<400> SEQUENCE: 43

Val Arg Leu Arg Ile Arg Val Arg Val Ile Arg Lys

<210> SEQ ID NO 44
<211> LENGTH: 9
<212> TYPE: PRT
<213> ORGANISM: Artificial Sequence
<220> FEATURE:
<223> OTHER INFORMATION: Chemically synthesized

<400> SEQUENCE: 44

Trp Phe Lys Met Arg Trp Trp Gly Arg
 1               5

<210> SEQ ID NO 45
<211> LENGTH: 9
<212> TYPE: PRT
<213> ORGANISM: Artificial Sequence
<220> FEATURE:
<223> OTHER INFORMATION: Chemically synthesized

<400> SEQUENCE: 45

Trp Lys Ile Val Phe Trp Trp Arg Arg
 1               5

<210> SEQ ID NO 46
<211> LENGTH: 9
<212> TYPE: PRT
<213> ORGANISM: Artificial Sequence
<220> FEATURE:
<223> OTHER INFORMATION: Chemically synthesized

<400> SEQUENCE: 46

Trp Lys Trp Leu Lys Lys Trp Ile Lys
 1               5

<210> SEQ ID NO 47
<211> LENGTH: 9
<212> TYPE: PRT
<213> ORGANISM: Artificial Sequence
<220> FEATURE:
<223> OTHER INFORMATION: Chemically synthesized

<400> SEQUENCE: 47

Trp Lys Trp Arg Val Arg Val Thr Ile
 1               5

<210> SEQ ID NO 48
<211> LENGTH: 9
<212> TYPE: PRT
<213> ORGANISM: Artificial Sequence
<220> FEATURE:
<223> OTHER INFORMATION: Chemically synthesized

<400> SEQUENCE: 48

Trp Arg Lys Phe Trp Lys Tyr Leu Lys
 1               5

<210> SEQ ID NO 49
<211> LENGTH: 9
<212> TYPE: PRT
<213> ORGANISM: Artificial Sequence
<220> FEATURE:
<223> OTHER INFORMATION: Chemically synthesized

<400> SEQUENCE: 49

Tyr Lys Phe Arg Trp Arg Ile Tyr Ile
 1               5

```
<210> SEQ ID NO 50
<211> LENGTH: 9
<212> TYPE: PRT
<213> ORGANISM: Artificial Sequence
<220> FEATURE:
<223> OTHER INFORMATION: Chemically synthesized

<400> SEQUENCE: 50

Tyr Arg Leu Arg Val Lys Trp Lys Trp
1               5

<210> SEQ ID NO 51
<211> LENGTH: 13
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (13)..(13)
<223> OTHER INFORMATION: C-terminal amido group

<400> SEQUENCE: 51

Ile Leu Arg Trp Lys Trp Arg Trp Arg Trp Arg Trp Arg
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (13)..(13)
<223> OTHER INFORMATION: C-terminal amido group

<400> SEQUENCE: 52

Lys Arg Trp His Trp Trp Arg Arg His Trp Val Val Trp
1               5                   10

<210> SEQ ID NO 53
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (9)..(9)
<223> OTHER INFORMATION: C-terminal amido group

<400> SEQUENCE: 53

Lys Arg Trp Trp Lys Trp Trp Arg Arg
1               5

<210> SEQ ID NO 54
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (9)..(9)
<223> OTHER INFORMATION: C-terminal amido group

<400> SEQUENCE: 54
```

```
Arg Arg Trp Trp Arg Trp Val Val Trp
1               5

<210> SEQ ID NO 55
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (9)..(9)
<223> OTHER INFORMATION: C-terminal amido group

<400> SEQUENCE: 55

Trp Lys Trp Leu Lys Lys Trp Ile Lys
1               5
```